US005639745A

United States Patent [19]
Dolle et al.

[11] Patent Number: 5,639,745
[45] Date of Patent: *Jun. 17, 1997

[54] FUSED-BICYCLIC LACTAMS AS INTERLEUKIN-1β CONVERTING ENZYME INHIBITORS

[75] Inventors: Roland E. Dolle, Pottstown; Prasad V. Chaturvedula, Exton; Tina Morgan Ross, Audubon; Stanley J. Schmidt, Chester Springs, all of Pa.

[73] Assignee: Sanofi, Paris Cedex, France

[*] Notice: The term of this patent shall not extend beyond the expiration date of Pat. No. 5,552,400.

[21] Appl. No.: 451,108

[22] Filed: May 25, 1995

Related U.S. Application Data

[62] Division of Ser. No. 255,276, Jun. 8, 1994, Pat. No. 5,552,400.

[51] Int. Cl.$^6$ ............ A61K 31/55; C07D 487/04; C07D 513/04; C07D 471/04

[52] U.S. Cl. .......... 514/183; 514/214; 514/221; 514/299; 514/306; 514/248; 514/227.2; 540/567; 540/593; 540/460; 540/461; 544/47; 544/235; 546/138; 546/183

[58] Field of Search ............ 540/567, 593, 540/460, 461; 544/47, 235; 546/138, 183; 514/221, 299, 306, 248, 214, 227.2, 183

[56] References Cited

U.S. PATENT DOCUMENTS

| | | | |
|---|---|---|---|
| 4,341,781 | 7/1982 | Hassall et al. | 424/250 |
| 4,399,136 | 8/1983 | Hassall et al. | 424/250 |
| 4,988,771 | 1/1991 | Angebauer et al. | 514/326 |

*Primary Examiner*—Matthew V. Grumbling
*Attorney, Agent, or Firm*—William J. Davis; Imre Balogh; Paul Dupont

[57] ABSTRACT

Disclosed are compounds, compositions and methods for inhibiting interleukin-1β protease activity. The compounds, bicyclic derivatives of aldehydes and α-substituted methyl ketones, have the formula (A) set out herein.

33 Claims, No Drawings

FUSED-BICYCLIC LACTAMS AS INTERLEUKIN-1β CONVERTING ENZYME INHIBITORS

This application is a division of application Ser. No. 08/255,276, filed Jun. 8, 1994, now U.S. Pat. No. 5,552,400.

BACKGROUND OF THE INVENTION

1. Field of the Invention

This invention relates to a series of novel bicyclic derivatives which exhibit in vitro and in vivo inhibition of interleukin-1β converting enzyme, to compositions containing the novel bicyclic derivatives and to methods for therapeutic utility. More particularly, the interleukin 1β converting enzyme inhibitors described in this invention comprise novel bicyclic derivatives of aldehydes and α-substituted methyl ketones which possess particular utility in the treatment of inflammatory and immune-based diseases of lung, central nervous system, and connective tissues.

2. Reported Developments

Interleukin 1β (IL-1β) protease (also known as interleukin-1β converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A., Proc. Nat. Acad. Sci., (1989), 86, 5227–5231 and Black, R. A.; Kronheim, S. R.; Sleath, P. R., FEBS Let., (1989), 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, acute and chronic myelogenous leukemia and osteoporosis (Dinarello, C. A.; Wolff, S. M., New Engl. J. Med., (1993), 328, 106). A naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., Nature, (1990), 343, 336–340; Eisenberg, S. P.; Evans, R. J.; Arend, W. P.; Verderber, E.; Brewer, M. T.; Hannum, C. H.; Thompson, R. C., Nature (1990), 343, 341–346; Ohlsson, K.; Bjork, P.; Bergenfeldt, M.; Hageman, R.; Thompson, R. C., Nature, (1990), 348, 550–552; Wakabayashi, G., FASEB, (1991), 338–343; Pacifici, R.; et al. Proc. Natl. Acad. Sci. (1989), 86, 2398–2402 and Yamamoto, I.; et al. Cancer Rsh (1989), 49, 4242–4246). The specific role of IL-1β in inflammation and immunomodulation is supported by the recent observation that the cowpox virus employs an inhibitor of ICE to suppress the inflammatory response of its host (Ray, C. A. et al, Cell, (1992), 69, 597–604).

The importance of these observations is well recognized by those skilled in the art and several workers have proposed and demonstrated in vivo the utility of ICE inhibitors in modifying certain IL-1β mediated disease states. Some have suggested the development and therapeutic use of a small molecule inhibitor of mature IL-1β formation. (See, e.g., Miller, D. K. et al. "The IL-1β Converting Enzyme as a Therapeutic Target" in Immunosuppressive and Antiinflammatory Drugs; Annals of the New York Academy of Sciences; Vol. 696, pp 133–148, 1993). The following review of the current state of the art in ICE research further supports such utility of ICE inhibitors:

1) WO 9309135, published 11 May 1993, teaches that peptide-based aspartic acid arylacyloxy-and aryloxymethyl ketones are potent inhibitors of ICE in vitro. These compounds also specifically inhibited ICE in the whole cell (in vivo) by their ability to inhibit the formation of mature IL-1β in whole cells. These ICE inhibitors also demonstrated utility in reducing fever and inflammation/swelling in rats.

2) Patients with Lyme disease sometimes develop Lyme arthritis. B. burgdorferi, the causative agent of Lyme disease, is a potent inducer of IL-1 synthesis by mononuclear cells. Miller et al. (Miller, L. C.; Lynch, E. A. Isa, S.; Logan, J. W.; Dinarello, C. A.; and Steere, A. C., "Balance of synovial fluid IL-1β and IL-1 Receptor Antagonist and Recovery from Lyme arthritis", Lancet (1993) 341; 146–148) showed that in patients who recovered quickly from Lyme Arthritis, the balance in synovial fluid of IL-1β and IL-1ra was in favor of IL-ra. When the balance was shifted in favor of IL-1β, it took significantly longer for the disease to resolve. The conclusion was that the excess IL-1ra blocked the effects of the IL-1β in the patients studied.

3) The IL-1 receptor antagonist, Antril (Synergen), possess significant antiinflammatory activity in patients with active rheumatoid arthritis. In multicenter Phase II dose ranging study, 175 patients received subcutaneous doses of antril at 20 mg, 70 mg and 200 mg. The antagonist was found to be most effective when taken daily. After three weeks of daily treatment, patients showed a decrease in joint swelling and less disease activity. A second Phase II clinical trial is scheduled to begin in 1994 (Scrip, NO 1873, 1993).

4) IL-1 is present in affected tissues in ulcerative colitis in humans. In animal models of the disease, IL-1β levels correlate with disease severity. In the model, administration of 1L-1ra reduced tissue necrosis and the number of inflammatory cells in the colon. See, Cominelli, F.; Nast, C. C.; Clark, B. D.; Schindler, R., Llerena, R.; Eysselein, V. E.; Thompson, R. C.; and Dinarello, C. A.; "Interleukin-1 Gene Expression, Synthesis, and Effect of Specific IL-1 Receptor Blockade in Rabbit Immune Complex Colitis" J. Clin. Investigations (1990) Vol. 86, pp, 972–980.

5) The IL-1 receptor antagonist, Antril (Synergen), possess significant antiinflammatory activity in patients with active rheumatoid arthritis. In a multicenter Phase II dose ranging study, 175 patients received subcutaneous doses of Antril at 20 mg, 70 mg and 200 mg seven times, three times or once per week. The antagonist was found to be most effective when taken daily. After three weeks of daily treatment, patients showed a decrease in joint swelling and less disease activity (Scrip, NO 1873, 1993).

6) IL-1ra supresses joint swelling in the PG-APS model of arthritis in rats. See Schwab, J. H.; Anderle, S. K.; Brown, R. R.; Dalldorf, F. G. and Thompson, R. C., "Pro- and Anti-Inflammatory Roles of Interelukin-1 in Recurrence of Bacterial Cell Wall-Induced Arthritis in Rats". Infect. Immun. (1991) 59; 4436–4442.

7) IL-1 ra shows efficacy in an small open-label human Rheumatoid Arthritis trial. See, Lebsack, M. E.; Paul, C. C.; Bloedow, C. C.; Burch, F. X.; Sack, M. A.; Chase, W., and Catalano, M. A. "Subcutaneous IL-1 Receptor Antagonist in Patients with Rheumatoid Arthritis", Arth. Rheum. (1991) 34; 545.

8) Soluble IL-1 receptor significantly reduces clinically the cutaneous late-phase allergic reaction. This was demostrated in a prospective, randomized, double-blind, placebo-controlled study on 15 allergic subjects. See, Mullarkey, M. F. et al. "Human Cutaneous Allergic Late-Phase Response is Inhibited by Soluble IL-1 Receptor", J. of Immunology, (1994) 152; 2033–2041.

9) IL-1 appears to be an autocrine growth factor for the proliferation of chronic myelogenous leukemia cells. Both IL-1 ra and sIL-1R inhibit colony growth in cells removed from leukemia patients. See, Estrov, Z.; Kurzrock, R.; Wetzler, M.; Kantarjian, H.; Blake, M.; Harris, D.; Gutterman, J. U.; and Talpaz, M., "Supression of Chronic Myelogenous Leukemia Colony Growth by Interleukin-1 (IL-1) Receptor Antagonist and Soluble IL-1 Receptors: a Novel Application for Inhibitors of IL-1 Activity". *Blood* (1991) 78; 1476–1484.

10) As in 6) above, but for acute myelogenous leukemia rather than chronic myelogenous leukemia. See, Estrov, Z.; Kurzrock, R.; Estey, E.; Wetzler, M.; Ferrajoli, A.; Harris, D.; Blake, M.; Guttermann, J. U.; and Talpaz, M. "Inhibition of Acute Myelogenous Leukemia Blast Proliferation by Interleukin-1 (IL-1) Receptor Antagonist and Soluble IL-1 Receptors". (1992) *Blood* 79; 1938–1945.

The IL-1 receptor antagonist, Antril (Synergen), possess significant antiinflammatory activity in patients with active rheumatoid arthritis. In multicenter Phase II dose ranging study, 175 patients received subcutaneous doses of antril at 20 mg, 70 mg and 200 mg. The antagonist was found to be most effective when taken daily. After three weeks of daily treatment, patients showed a decrease in joint swelling and less disease activity. A second Phase II clinical trial is scheduled to begin in 1994 (Scrip, NO 1873, 1993).

An effective therapy has yet to be fully developed commercially for the treatment of IL-1β mediated inflammatory diseases. Consequently, there is a need for therapeutic agents effective in the treatment and prevention of these diseases.

SUMMARY OF THE INVENTION

We describe in this invention non-peptide based inhibitors of ICE, specifically where fused bicyclic lactam peptidomimetics serve as recognition elements for ICE. One of the most potent classes of ICE inhibitors described in the literature is the tripeptide i, Z-Val-Ala-Asp-CH$_2$-X (FIG. 1: where X=2,6-dichlorobenzoyloxy; Dolle, R. E. et al, J. Med. Chem. (1994), 37, 563) and the related tripeptides described by Thornberry (Thornberry, N. A. et al., Biochemistry (1994), 33, 3934). One well known disadvantage of peptide-based inhibitors is their potential to be extensively metabolized by the body and to be poorly bioavailable when administered orally. By contrast, one significant advantage of peptidomimetic-based inhibitors versus their peptide counterparts is that in vivo metabolism and excretion of such peptidomimetic agents are greatly attenuated, thereby leading to enhanced oral bioavailability of these compounds in animals and humans (Humphrey, M. J. and Ringrose, P. S., "Peptides and Related Drugs: A Review of Their Absorption, Metabolism, and Excretion", *Drug Metabolism Reviews*, (1986), 17, 283–310; Plattner, J. J. and Norbeck, D. W. "Obstacles to Drug Development from Peptide Leads", *Drug Discovery Technologies*, (1990), Chapter 5, 92–126, C. R. Clark and W. H. Moos, eds.; Horwood: Chichester, U.K).

It is for this reason that researchers seek out peptidomimetics to act as surrogates for the peptide portion of pharmacologically active agents. The [7,6]-fused bicyclic lactam present in ii (FIG. 2) is such a peptidomimetic for the P3–P2 (Val-Ala) peptide portion of inhibitor i. (FIG. 1). Furthermore, the [7,6]-fused bicyclic system locks the ψ, ø angles about the amide P3–P2 amide bond in a fixed conformation. Hence, this invention relates to the discovery of a "bio-active" conformation favorable to ICE.

The bicyclic lactam iii (FIG. 3) is a rigid system with fixed ψ, ø angles. The rigidity of the system has been confimed by X-ray crystallography (Attwodd, M. R.; et al., *J. Chem. Soc.* Perkin Trans. I (1986), 1011–1019). The ψ angle has been established to be 163.9°. Logically, by virtue of the rigid bicyclic nature of the fused ring system, any other [7,6]-bicyclic lactam derivative or an analog of iii will have ψ, ø angles closely approximating those found in iii and the bioactive conformation needed for high affinity binding to ICE as shown in ii. It is for this reason we state then that any [7,6]- or the related [8,6]-, [7,5]- and [8,5] bicyclic lactam rings and derivatives and analogs thereof, will potentially have the property to act as a substitute for iii. Thus, when they are incorporated into an ICE inhibitor, these peptidomimetics will be active against the enzyme. Examples of lactam rings iv–xii whose synthesis are described in the art and which represent derivatives and analogs of iii are presented in FIG. 3.

Furthermore, the stereochemistry about the carbon atoms to which are attached the —NH— and —CO— functional groups as shown in structures iii–xii (FIG. 3) should be "S" to acheive maximal potency against ICE. That is to say both the —NH— and —CO— functional groups should be up and on the same face of the bicyclic lactam ring.

FIG. 1

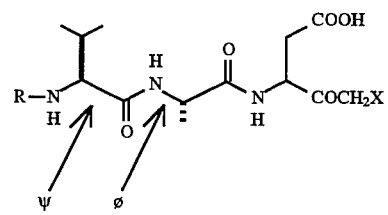

Peptide-based ICE inhibitor (Dolle, R. E. et al., J. Med. Chem (1994) 37, 563)

FIG. 2

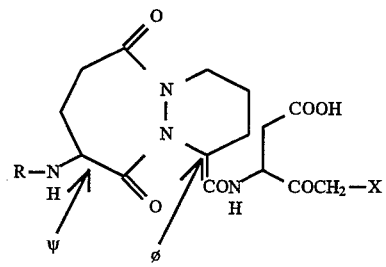

[7,6]-Bicyclic lactam-based ICE inhibitor (the invention)

FIG. 3

The [7,6]-bicyclic lactam peptidomimetic iii and the related bicyclic lactam peptidomimetics iv–xii:

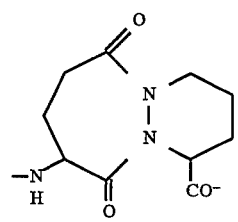

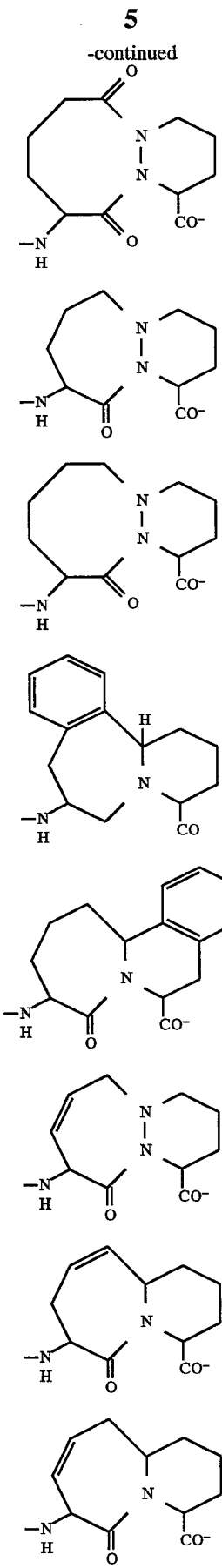

According to the present invention, there is provided a compound of the formula (A) or a pharmaceutically acceptable salt thereof:

$$Z-\underset{H}{N}-Y \quad (A)$$

wherein:

$$Y = \underset{R^1}{\overset{COR^2}{\diagdown}}\!\!\!\!\!\!\!\!\!\!\!\!\!\!\!\!\underset{N}{\diagup}\!\!\!\!\underset{H}{\diagdown}\!\!\!\!\underset{NH_2}{\diagup}\!\!\!\!\underset{O}{\diagdown}\quad \text{or} \quad \underset{R^1}{\overset{COR^2}{\diagdown}}\!\!\!\!\!\!\!\!\!\!\!\!\!\!\!\!\underset{O}{\diagdown}R^3$$

and when $R_2$=OH then Y can also be equal to:

$$\underset{HO}{\overset{R^1}{\diagdown}}\!\!\!\!\!\!\!\!\!\!\!\!\!\!\!\!\underset{R^3}{\diagup}\!\!\!\!\underset{O}{\diagdown}$$

wherein
n=0,1;
$R^1$=H or deuterium;
$R^2$=$OR^4$ or NHOH;
$R^4$=H, alkyl, cycloalkyl, aralkyl;
$R^3$=H, $(CR^8R^9)_{0-6}CF_3$, $(CR^8R^9)_{0-6}CF_2CF_3$, $(CR^8R^9)_{0-6}COOR^5$, $(CR^8R^9)_{0-6}$ $CONR^6R^7$, $CF_2(CR^8R^9)_{0-6}$aryl, $CF_2(CR^8R^9)_{0-6}$heteroaryl, $CF_2(CR^8R^9)_{0-6}$alkyl, $CHN_2,CH_2R^{10}$, $COR^5$;
wherein
$R^5$=H, alkyl, cycloalkyl, aryl, aralkyl, heteroaryl, heteroaralkyl;
$R^6$ and $R^7$ are independently selected from H, alkyl, cycloalkyl, aryl, aralkyl, heteroaryl, heteroaralkyl and where $R^6$ and $R^7$ are taken together can be a 3-,4-,5-,6- or 7-membered carbocyclic ring.
$R^8$ and $R^9$ are independently H, or alkyl;
$R^{10}$=alkyl, aryl, aralkyl, heteroaryl, heteroarakyl, H, halo, $SR^5$, $SR^5R^6$, $O(CO)_{0-1}$aryl, $O(CO)_{0-1}$heteroaryl, $OP(O)R^{11}R^{12}$,

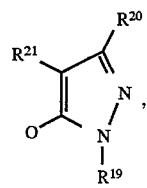

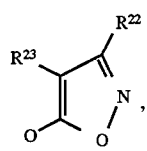

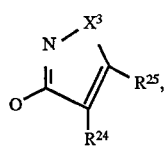

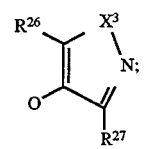

$R^{11}$ and $R^{12}$ are optionally selected from H, OH, alkyl, cycloalkyl, aryl, aralkyl, heteroaryl, heteroaralkyl, alkoxy, aroxy, aralkyloxy, heteroaroxy, heteroaralkyloxy;

$R^{13}$=H, alkyl, aryl, aralkyl;

$R^{14}$ and $R^{15}$ are optionally selected from H, alkyl, aryl, or when taken together $R^{14}$ and $R^{15}$ is an aryl ring;

$X^1$=O, S, $NR^{28}$ where $R^{28}$=H, alkyl, aryl, aralkyl, heteroaryl, heteroaralkyl;

$R^{16}$=H, Cl, alkyl, $(CR^8R^9)_{0-6}$-aryl;

$R^{17}$ and $R^{18}$ are independently H or alkyl;

$X^2$=$CH_2$, O, $NR^{28}$;

$R^{19}$=H, alkyl, cycloalkyl, alkylcycloalkyl, aryl, aralkyl, heteroaryl and heteroaralkyl;

$R^{20}$=H, alkyl, $CF_3$, $CF_2CF_3$, $COOR^5$, $CONR^6R^7$, cycloalkyl, alkylcycloalkyl, aryl, aralkyl, heteroaralkyl, heteroaryl and where $R^{21}$=H or alkyl;

$R^{22}$, $R^{23}$, $R^{24}$, $R^{25}$, $R^{26}$, and $R^{27}$ are independently selected from H, alkyl, cycloalkyl, alkylcycloalkyl, aryl, aralkyl, heteroaryl, heteroaralkyl and $R^{29}$; and where $R^{24}$ and $R^{25}$ when taken together may be aryl or heteroaryl;

$X^3$=O,S;

$R^{29}$=F, Cl, $CF_3$, $CF_2CF_3$, $(CF_2)_{0-3}$—H, $COOR^5$, $CONR^{30}R^{31}$, where $R^{30}$ and $R^{31}$ are optionally selected from $R^6$ and $R^7$,

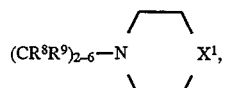

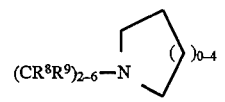

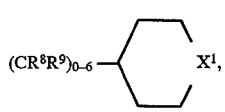

Z=

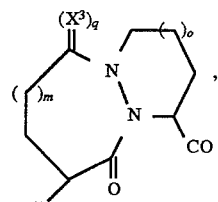

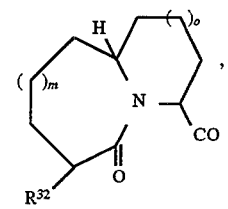

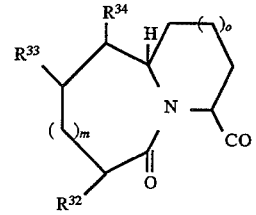

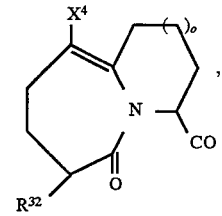

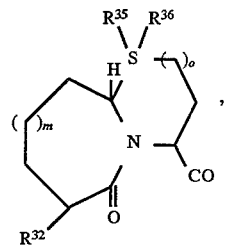

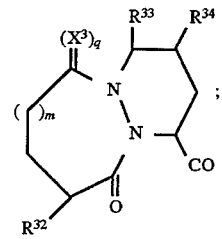

wherein q=0, 1;

m=0,1,2,3;

o=0,1,2;

$X^4$=H, alkylthio;

$R^{32}$ = 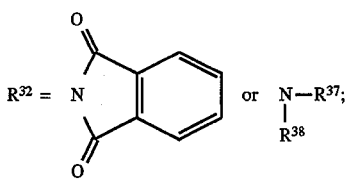 or N—$R^{37}$
          |
          $R^{38}$ $R^{33}$ and $R^{34}$ are optionally H, alkyl, aryl or when taken together, $R^{33}$ and $R^{34}$ are aryl, heteroaryl, or a double bond; $R^{35}$ and $R^{36}$ are optionally an oxygen atom or no bond; $R^{37}$=H, alkyl;
$R^{38}$=independently selected from H, alkyl, aryl, aralky, heteroaryl, heteroaralkyl,
$R^{40}$—$SO_2$, $R^{41}$—CO, $R^{50}$O—CO, $R^{51}NR^5$—CO;
wherein $R^{40}$=$R^5$ or $HNR^5$;
$R^{41}$=alkenyl, aralkenyl, heteroaralkenyl, alkynyl, aralkynyl, heteroaralkynyl, $R^{42}$—$OCOR^5$, $R^{43}$—$COR^5$, $R^{42}$—$NR^{47}C$(=$NR^6$)$R^5$, $R^{42}$—$NR^{47}$(=$NR^6$)$NR^5$, $R^{42}$—$SR^5$, $R^{42}$—S$(CR^8R^9)_{1-6}COOR^{47}$, $R^{42}$—S$(CR^8R^9)_{1-6}CONR^{47}R^{48}$, $R^{42}$—$OR^5$, $R^{42}$—$O(CR^8R^9)_{1-6}COOR^{47}$, $R^{42}$—$O(CR^8R^9)_{1-6}CONR^{47}R^{48}$, $R^{42}$—$NR^5SO_2R^6$, $R^{43}$—$R^{44}$, $R^{43}$—$R^{45}$, $R^{43}$—$R^{46}$, $R^{43}$—$NR^{47}R^{48}$, $R^{42}$—OH, $R^{43}$—$CF_3$;
wherein $R^{42}$=$(CR^8R^9)_{1-7}$ and $R^{43}$=$(CR^8R^9)_{0-6}$;
$R^{44}$=H, alkyl, —$(CH_2)_{0-4}$-cycloalkyl;

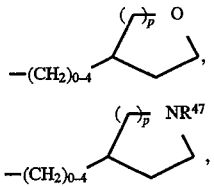

aryl, heteroaryl, aralkyl, heteroaralkyl, —$(CH_2)_{2-6}$—$R^{49}$;
wherein p=1–4;
$R^{49}$=alkoxy, $CH_2F$, $CHF_2$, $CF_3$, $CF_2CF_3$, OH, $COOR^{47}$, $CONR^{47}R^{48}$, or $NR^{47}R^{48}$;
wherein $R^{48}$ is independently H, alkyl, aryl, aralkyl, heteroaryl, heteroaralkyl, $CH_2CH_2$O-alkyl and C(O)13 $R^{49}$;
$R^{47}$ is independently H, alkyl, cycloalkyl, aryl, aralkyl, heteroaryl and heteroaralkyl; and when $R^{47}$ and $R^{48}$ are taken together, they can equal a five, six or seven membered ring of the type:

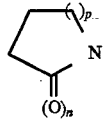

where p=1–4 and n=0–1;
$R^{49}$ is alkyl, aryl, aralkyl, heteroaryl and heteroaralkyl;

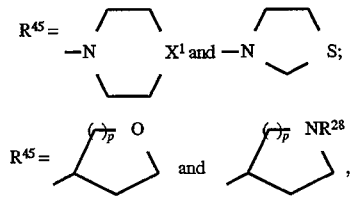

where p-1–4;
$R^{50}$ and $R^{51}$=independently selected from alkyl, $R^{43}$-cycloalkyl, aryl, aralkyl, heteroaryl, heteroaralkyl, $R^{42}$-alkenyl, $R^{42}$-heteroaralkenyl, $R^{42}$-alkynyl, $R^{42}$-aralkynyl, $R^{42}$-heteroaratkynyl, $R^{43}$—$R^{46}$, $R^{42}$—$R^{49}$, $R^{52}$—$R^{45}$, $R^{42}$—$COOR^{47}$, $R^{42}$—$CONR^{47}R^{48}$, $R^{52}$—$OCOR^5$, $R^{52}$—$COR^5$, $R^{52}$—$NR^{47}C$(=$NR^6$)$R^6$, $R^{52}$—$NR^{47}$(=$NR^6$)$NR^5$, $R^{52}$—$SR^5$, $R^{52}$—$S(CR^8R^9)_{1-6}COOR^{47}$, $R^{52}$—$S(CR^8R^9)_{1-6}CONR^{47}R^{48}$, $R^{52}$—$OR^5$, $R^{52}$—$O(CR^8R^9)_{1-6}COOR^{47}$, $R^{52}$—$O(CR^8R^9)_{1-6}CONR^{47}R^{48}$, $R^{52}$—$NR^5SO_2R^6$, $R^{52}$—$R^{44}$, $R^{52}$—$NR^{47}R^{48}$,
where $R^{52}$=$(CR^8R^9)_{2-6}$;

As used herein, the term "pharmaceutically acceptable salts" include the acid and base addition salts.

The term "acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

As employed above and throughout the disclosure, the following terms, unless otherwise indicated, shall be understood to have the following meanings:

"Alkyl" is defined as a saturated aliphatic hydrocarbon which may be either straight- or branched-chain. Preferred groups have no more than about 12 carbon atoms and may be methyl, ethyl, propyl, and so on and structural isomers of propyl, butyl, pentyl, hexyl, octyl, nonyl, decyl, undecyl, dodecyl.

"Cyclolalkyl" is defined as a saturated cyclic aliphatic hydrocarbon containing from at least 3 to as many as 8 carbon atoms. Preferred groups include cyclopropyl, cyclobutyl, cyclopentyl, cyclohexyl, cycloheptyl and cyclooctyl.

"Aryl" is defined as a phenyl or naphthyl ring or a substituted phenyl or naphthyl ring wherein one or more of the hydrogen atoms has been replaced by the same or different substituents as selected from $R^{43}$—$R^5$, $R^{43}$—CN, $R^{43}$—$NO_2$, $R^{43}$—halo, $R^{43}$—$OR^5$, $R^{43}$—$R^{38}$, $R^{43}$—$NR^5OH$, $R^{43}$—$CF_3$, $R^{43}$—$CF_2CF_3$, $R^{43}$—$COOR^5$, $R^{43}$—$CONR^6R^7$, $R^{43}$—$CF_2(CR^8R^5)_{0-6}$heteroaryl, $R^{43}$—$CF_2(CR^8R^9)_{0-6}$aryl, $R^{43}$—$CF_2(CR^8R^9)_{0-6}$alkyl, $R^{43}$—$CON^{47}R^{48}$, $R^{43}$—$CON^{30}R^{31}$, $R^{43}$—$NR^8R^{38}$, $R^{43}$—P(O)(OH)($OR^5$), alkenyl, aralkenyl, heteroaralkenyl, alkynyl, aralkynyl, heteroaralkynyl, $R^{43}$—$SO_2R^5$, $R^{43}$—$SO_2NR^6R^7$, $R^{43}$—$NR^5SO_2R^{53}$, $R^{43}$—$NR^5SO_2R^{53}$, $R^{43}$—$SO_2$—$R^{42}$—

COOR$^{47}$, R$^{43}$—SO$_2$—R$^{42}$—CONR$_6$R$_7$, R$^{43}$—OCOR$^5$, R$^{43}$—COR$^5$, R$^{43}$—NR$^{47}$C(=NR$^6$)R$^5$, R$^{43}$—NR$^{47}$C(=NR$^6$)R$^5$, R$^{43}$—S—R$^{43}$—R$^5$, R$^{43}$—S—R$^{42}$—COOR$^{47}$, R$^{43}$—O—R$^{42}$—COOR$^{47}$, R$^{43}$—S—R$^{42}$—CONR$^{47}$R$^{48}$, R$^{43}$—O—R$^{43}$—R$^5$, R$^{43}$—O—R$^{52}$—R$^{45}$, R$^{43}$—S—R$^{52}$—O—R$^{46}$, R$^{43}$—S—R$^{52}$—R$^{45}$, R$^{43}$—S—R$^{46}$, R$^{43}$—R$^{45}$, R$^{43}$—R$^{46}$; where R$^{53}$=alkyl, cycloalkyl, aryl, aralkyl, heteroaryl, heteroalkyl.

"Heteroaryl" is defined as an unsubstituted or an optionally substituted mono- or bicyclic ring system of about 5 to about 12 carbon atoms and where each monocyclic ring may possess from 0 to about 4 heteroatoms, and each bicyclic ring my possess about 0 to about 5 heteroatoms selected from N, O, and S provided said heteroatoms are not vicinal oxygen and/or sulfur atoms and where the substituents, numbering from 0 to about 5 may be located at any appropriate position of the ring system and are optionally selected from the substituents listed for those described for aryl. Examples of such mono- and bicyclic ring systems which are by no means meant to limit the scope of this invention, including benzofuran, benzothiophene, indole, benzopyrazole, coumarin, isoquinoline, pyrrole, thiophene, furan, thiazole, imidazole, pyrazole, triazole, quinoline, pyrimidine, pyridine, pyridone, pyrazine, pyridazine, isothiazole, isoxazole and tetrazole.

"Aralkyl" refers to an alkyl group substituted by an aryl radical. For example, benzyl.

"Heteroaralkyl" refers to an alkyl group substituted by a heteroaryl radical. For example, (4-pyridyl)methyl.

"Alkoxy" refers to an O-atom substituted by an alkyl radical. For example methoxy, ethoxy, phenoxy, benzyloxy.

"Halo" means iodo, bromo, chloro, and fluoro.

The designation "(CR$^8$R$^9$)$_{2-4}$" refers to an alkyl linkage composed of at least 2 but not more than 4 carbon atoms where said carbon atoms are independently substituted with radicals described by R$^8$ and R$^9$. Examples of such linkages include but are not limited to ethyl, propyl, butyl, 2-methylethyl-(MeHCCH$_2$—), and 2,2-dimethylethyl (Me$_2$CCH$_2$—).

"Aroxy" refers to an O-atom substituted by an aryl radical. For example phenoxy.

"Heteroaroxy" refer to an O-atom substituted by a heteroaryl radical. For example pyridinyloxy.

"Alkenyl" refers to an unsaturated hydrocarbon which may be either straight- or branched-chain and have one or more double bonds. Preferred groups have no more than about 12 carbon atoms and may be ethenyl, propenyl, hexadienyl, and so on and structural isomers thereof.

"Alkynyl" refers to an unsaturated hydrocarbon which may be either straight- or branched-chain and have one or more triple bonds. Preferred groups have no more than about 12 carbons atoms and may be ethyl, propynyl, 4-methylpentynl and so on and structure isomers thereof.

"Aralkenyl and heteroaralkenyl" refer to an alkenyl group substituted by an aryl or heteroaryl ring. For example ArCH=CH—, ArCH$_2$CH$_2$CH$_2$HC=C—, CH$_3$CH$_2$CH(Ar)CH$_2$CH$_2$CH=CH—, and so on.

"Aralkynyl and heteroaralkynyl" refer to an alkynyl group substituted by an aryl or heteroaryl ring. For example ArC≡C—,ArCH$_2$CH$_2$CH$_2$C≡C— and so on.

The present invention also concerns the pharmaceutical composition and method of treatment of IL-1β protease mediated disease states or disorders in a mammal in need of such treatment comprising the administration of IL-1β protease inhibitors of formula (I) as the active agent. These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseass, such as hypersensitivity; auto-immune diseases, such as multiple sclerosis; bone diseases; and certain tumors and leukemias.

The present invention has particular utility in the modulation of processing of IL-1β for the treatment of rheumatoid arthritis. Levels of IL-1β are known to be elevated in the synovial fluid of patients with the disease. Additionally, IL-1β stimulates the synthesis of enzymes believed to be involved in inflammation, such as collagenase and PLA2, and produces joint destruction which is very similar to rheumatoid arthritis following intra-articular injection in animals.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectally, buccally (including sublingually), transdermally or intranasally. The most suitable route in any given case will depend upon the use, the particular active ingredient, and the subject involved. The compound or composition may also be administered by means of controlled-release, depot implant or injectable formulations as described more fully herein.

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to mg/kg to about 10 mg/kg.

The exact dose and regimen for administration of these compounds and compositions will necessarily be dependent upon the needs of the individual subject being treated, the type of treatment, and the degree of affliction or need, In general, parenteral administration requires lower dosage than other methods of administration which are more dependent upon absorption.

A further aspect of the present invention relates to pharmaceutical compositions comprising as an active ingredient a compound of the present invention in admixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitar monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences*, 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

DETAILED DESCRIPTION OF THE INVENTION

The compounds of this invention were prepared by using the general synthetic methods as described in Schemes 1, 2, 3, 4 and 5. Z-Asparatic acid α-bromomethyl ketone (Scheme 1; Formula 1; Z=benzyloxycarbonyl) is treated with an alcohol or a carboxylic acid in the presence of KF using DMF as a solvent to give the α-substituted Z-aspartic acid methyl ketones (Formula 2). The preparation of bromide (Formula 1) and its conversion to compounds of Formula 2 is accomplished using the methods as described by A. Krantz, et al. (Biochemistry, (1991), 30, 4678–4687). Subsequently, the Z-group is removed to generate an N-terminal amine (Formula 3) under hydrogenolytic conditions. The reagents and conditions typically used to carry out the hydrogenolyic removal of the Z-group are hydrogen gas, ambient temperature and pressure, 5% palladium on carbon as the catalyst in an alcoholic solvent e.g., methanol optionally containing two equivalents of hydrochloric acid. It is not necessary to purify the intermediate free amine (or the hydrochloride salt if hydrochloric acid is used in the hydrogenolysis), though this material needs to be dry and free of alcohol for the subsequent coupling reaction to proceed in good yield. The amine (Formula 3) so obtained is then condensed with the bicyclic carboxylic acid (Formula 4) to yield intermediates of Formula 5. It is generally necessary to first activate the bicyclic carboxylic acid as an acid chloride or mixed anhydride and then react it with the free amine (or hydrochloride salt) in the presence of an organic base, e.g., N-methylmorpholine. Alternatively, coupling the bicyclic carboxylic acid with the intermediate amine is conducted using amide coupling reagents/ conditions employed in peptide coupling chemistry ("The Practice of Peptide Synthesis." M. Bodanszky, Springer-Verlag, N.Y., 1984; The Peptides. Vol 1–3, E. Gross and J. Meienhofer, Eds. Academic Press, N.Y., 1981). The remaining synthetic transformation to generate the ICE inhibitors is the hydrolysis of the t-butyl ester function. This is conducted by exposing the t-butyl ester (Formula 5) to a 25% solution of trifluoroacetic acid (TFA) in methylene chloride at 25° C. The de-esterification is usually complete in 3 h. Removal of the volatile TFA and organic solvent affords the aspartic acid (Formula 6). The yield of the reaction is quantitative in most instances, providing the t-butyl ester starting material is of high purity. Purification, if required, can be performed by recrystallization or chromatographic techniques which are well known to those skilled in the art. The concentration of TFA may range form 5%–100% and other organic solvents may be used such as chloroform. Also, a solution of three molar anhydrous hydrochloric acid in ethyl acetate may be used in place of the TFA-methylene chloride solution with equal efficiency.

Scheme 2 outlines the synthesis of the aldehyde containing bicycles. The starting material for their synthesis is the aspartyl semicarbazone (Formula 7). The Z-group is removed via standard hydrogenation conditions to yield the corresponding amine (Formula 8). This is then coupled to the bicyclic carboxylic acid (Formula 4) using coupling conditions analogous to those described above. A double de-protection is required to free the beta carboxylic acid (trifluoroacetic acid) and the alfa aldehyde (37% aqueous formaldehyde, acetic acid, methanol) yielding compounds of Formula 10.

Scheme 3 outlines an alternate synthetic method for introducing $R^{38}$ groups onto the bicyclic amino function further enhancing the scope of this invention. Bicycles either as their free acids, esters or aspartic acid amides which contain a Z-group (Formula 11) may be subjected to hydrogenolysis conditions (similar to those described above) to yield the corresponding amino bicycles (Formula 12). The amine moiety may be reacted with acid chlorides, activated carboxylic acids (conditions analogous to those used to couple Formula 3 and 4 as described in Scheme 1 above), or sulfonyl chlorides, or isocyanates to afford $R^{38}$ containing bicyclic lactams with structural diversity in $R^{38}$.

The bicyclic lactam of Formula 4 (Scheme 4) was prepared using known methods, see: Attwood; et al., CA100 (17):139158j CA, "Bicyclic Carboxylic Acids and their Alkyl and Aralkyl Esters", GB 82-13850 820512; and GB 83-5505 830228; Hassail, C. H. et al; *J. Chem. Soc. Perkin I*, 1451–1454, (1979), and Hale, K. J. et al.; *Tetrahedron Letters* (1992), 33, 7613–7616. The ester was treated with hydrazine under standard conditions (See, Green, T. W.; "Protective Groups in Organic Synthesis"; John Wiley & Sons, 1981) to give the free amine (Formula 15) in high yield. This material was reacted with benzyloxycarbonyl chloride and then TFA also using standard conditions (Formula 15→Formula 16→Formula 4). The details for this series of reactions are given below.

In Scheme 5, the synthesis of other bicyclic lactam derivatives are presented. Bicyclic lactams of Formulas 17–26 are known in the art. For the synthesis of Formula, 17, 18 and 19, see (Hoffmann-La Roche patent); for the synthesis of formula 20, see Flynn, G. A.; et al., *J. Amer. Chem. Soc.* (1987). 109, 7914–7915; for the synthesis of the compound of formula 21, see Robl, J. A.; et al, *J. Amer. Chem. Soc.*, (1994), 116, 2348–2355; for the synthesis of compounds of formula 22–24 see, Robl, J. A. *Tetrahedron Letters* (1994), 35. 393–396; for the synthesis of compounds of formulas 25 and 26, see Wyvratt, M. J. et al. in "Peptides Structure and Function", Proceeding of the Eighth American Peptide Symposium, Eds. V. J. Hruby and D. H. Rich, pages 551–554, 1983 and Wyvratt, Matthew J., Jr. (Merck and Co., Inc.) S. African ZA 85 07,527 (Cl.C07D), 28 May 1986, U.S. application Ser. No. 655818.01 October 1984.

By analogy with the chemistry presented in Schemes 1–4, practitioners skilled in the art would readily see that Formulas 17–26 can be transformed into bicyclic lactam inhibitor classes Formulas 27–36. The phthaloyl protecting group on the amino group can be treated with hydrazine analogous to the Formula 14→15 transformation in Scheme 4. Indeed such a transformation is reported for Formulas 17–26 in the literature (see previous list of references). This would yield a free amine or its salt which could be treated with PhCH$_2$OCOCl or any reactive group to give R$^{38}$-containing inhibitors as in formulas 28–37. As for hydrolysis of the ester function in Formulas 17–26, TFA can be used for cases where the esters are t-butyl esters (analogous to Formula 16, Scheme 4). In cases where the ester is an ethyl or methyl ester, aqueous hydroxide anion can be used to effect hydrolysis. After the ester is hydrolyzed to the corresponding acid, the acid functionality in turn is used in coupling to the aspartic acid derivatives (analogous to Formula 4→5 (Scheme 1) and Formula 4→9 (Scheme 2)) yielding compounds of the type described by Formulas 27–36.

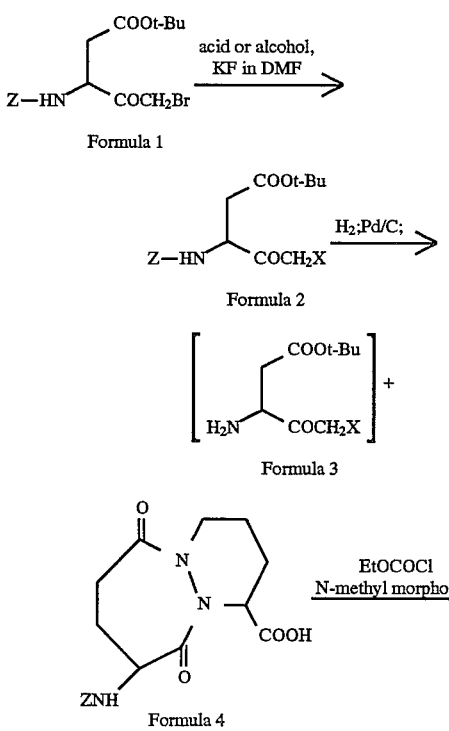

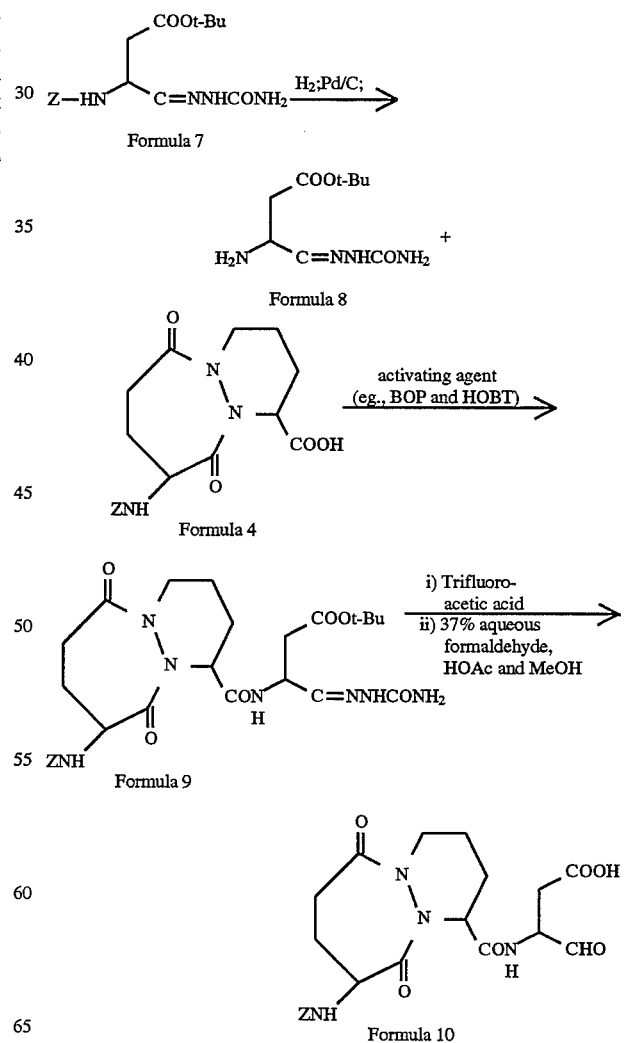

17

SCHEME 3

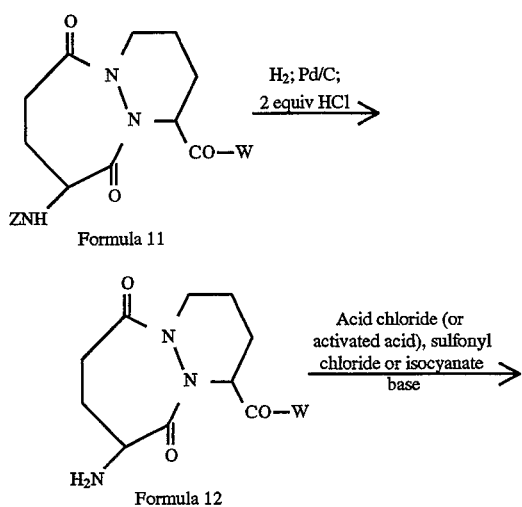

Formula 11 → (H₂; Pd/C; 2 equiv HCl)

Formula 12 → (Acid chloride (or activated acid), sulfonyl chloride or isocyanate base)

Formula 13

SCHEME 4

Formula 14 → (H₂NNH₂)

[Formula 15] → (PhCH₂OCOCl)

Formula 16 → (ester hydrolysis (in this case use TFA))

18

-continued
SCHEME 4

Formula 4

SCHEME 5

The following bicyclic ring systems are known in the literature and by analogy with Schemes 1, 2, 3, and 4, the following classes of compounds can be prepared:

Formula 17 →

Formula 27

Formula 18 →

19
-continued
SCHEME 5
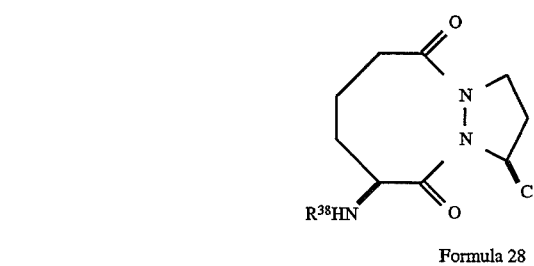
Formula 28
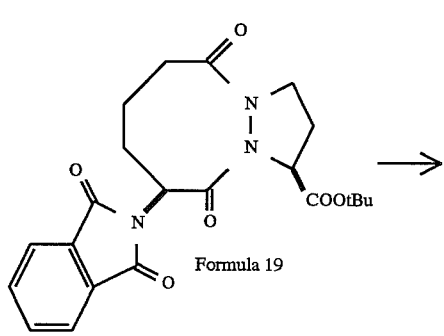
Formula 19
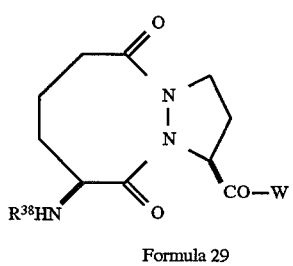
Formula 29
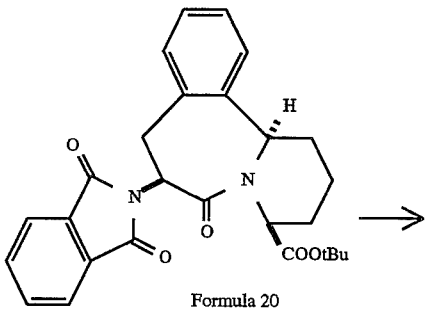
Formula 20
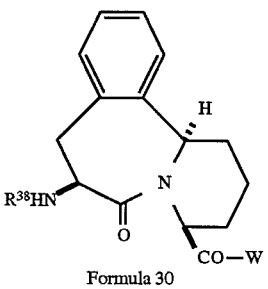
Formula 30
20
-continued
SCHEME 5
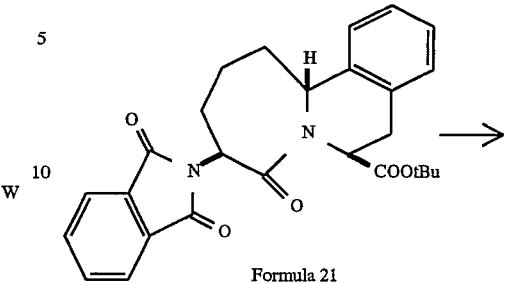
Formula 21
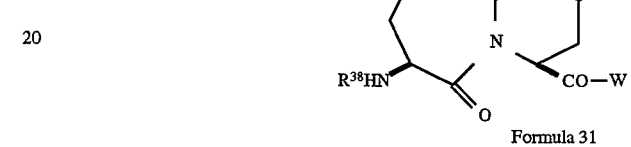
Formula 31
Formula 22
Formula 32
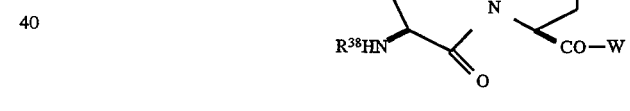
Formula 23
Formula 33

-continued
SCHEME 5

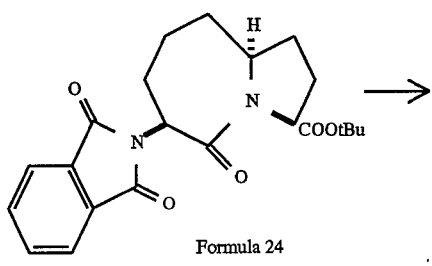

Formula 24

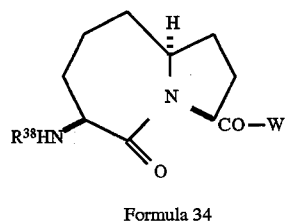

Formula 34

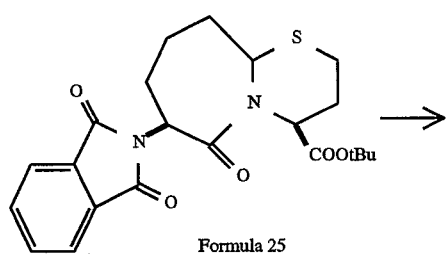

Formula 25

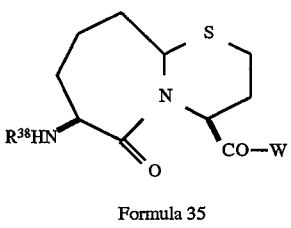

Formula 35

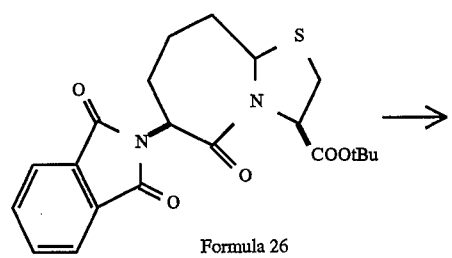

Formula 26

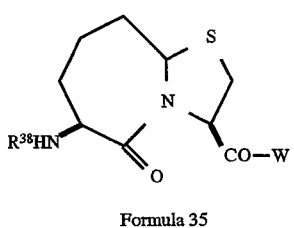

Formula 35 where

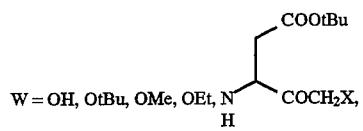

W = OH, OtBu, OMe, OEt,

-continued
SCHEME 5

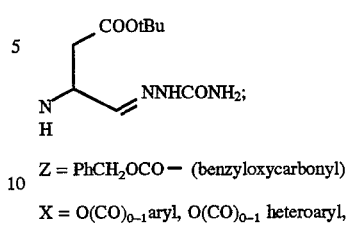

Z = PhCH$_2$OCO— (benzyloxycarbonyl);

X = O(CO)$_{0-1}$aryl, O(CO)$_{0-1}$ heteroaryl,

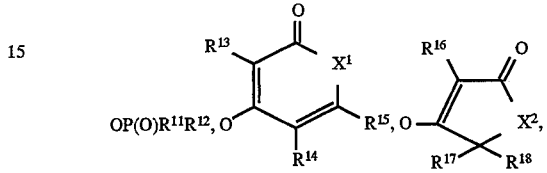

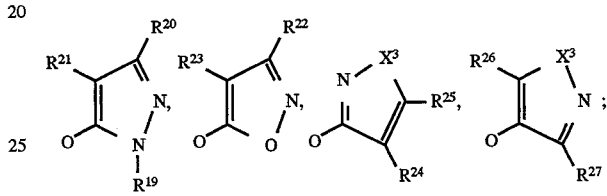

where aryl, heteroaryl, $X^1$, $X^2$, $X^3$ and $R^{38}$ are as previously described.

SYNTHESIS OF INTERMEDIATES OF FORMULAS 16 AND 4

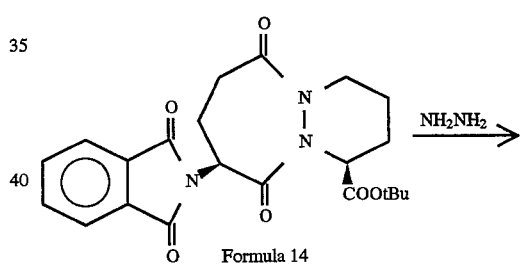

Formula 14

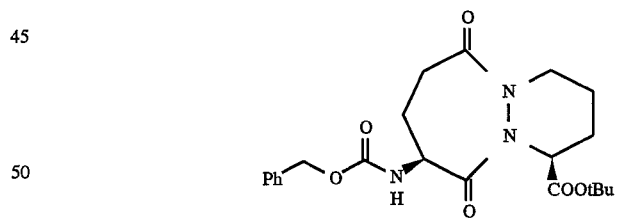

Formula 16

A suspension of (1S, 9S)-t-butyloctahydro-10-oxo-9-phthalimido-6H-pyridazino [1,2-a][1,2]diazepine-1-carboxylate (Formula 14:4.13 g, 10 mmol) in ethanol (41.3 mL) was treated with hydrazine hydrate (1.1 g, 22 mmol). After the mixture had been stirred for 1 h at ambient temperature, the solvents were evaporated and the residue azeotroped with toluene. 2M aqueous acetic acid (41.3 mL) was and the mixture stirred for 3 h and then filtered. The filtrate was basified with anhydrous sodium carbonate and 100 mL of dichloromethane was added. Then anhydrous sodium carbonate (1.59 g, 15 mmol) and benzyl chloroformate (2.14 mL, 15 mmol) at room temperature were added and the reaction mixture was stirred for 3 h. The organic phase was separated, dried (Na$_2$SO$_4$) and the product (Formula 16) purified by flash chromatography using 50% ethyl acetate-hexane.

$^1$H NMR (300 MHz,CDCl$_3$) δ7.4–7.25 (m, 5H), 5.58 (d, 1H), 5.24 (m, 1H), 5.08 (s, 2H), 4.7–4.48 (m, 2H), 3.56–3.4 (m, 1H), 2.84–2.63 (m, 2H), 2.4–2.3 (m, 1H), 2.28–2.20 (m, 1H), 1.86–1.44 (m, 4H), 1.41 (s, 9H).

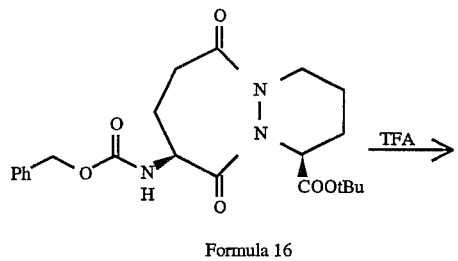

Formula 16

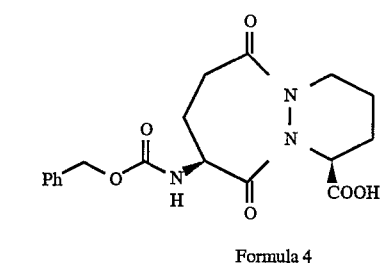

Formula 4

To a stirred solution of t-butyl ester (Formula 16:3.88 g, 9 mmol) in methylene chloride (30 mL) was added trifluoroacetic acid (50 mL) and stirring continued for 5 h. The solvents were evaporated and azeotroped twice with toluene (30 mL) to give the product (Formula 4) in almost quantitative yield. Mass spectrum: 376 (M+H)

The following further illustrate the compounds of the present invention.

EXAMPLE 1

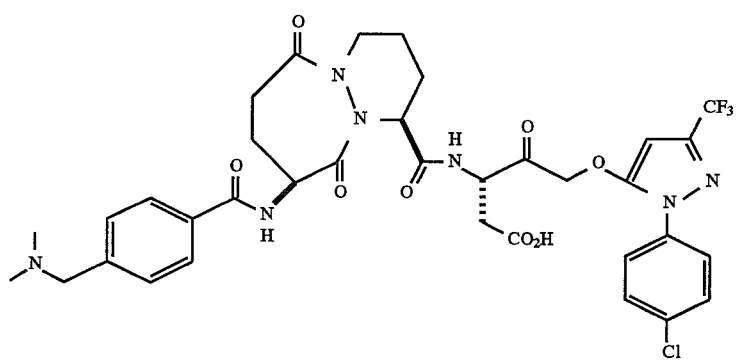

[9-(4-Dimethylaminomethyl)benzoylamino)octahydro-6, 10-dioxo-6H-pyridazino[1,2a][1,2]diazepine-1-formoyl]-L-aspartic acid 5-(1-4-chlorophenyl)-3-trifluoromethyl) pyrazoloxymethyl ketone

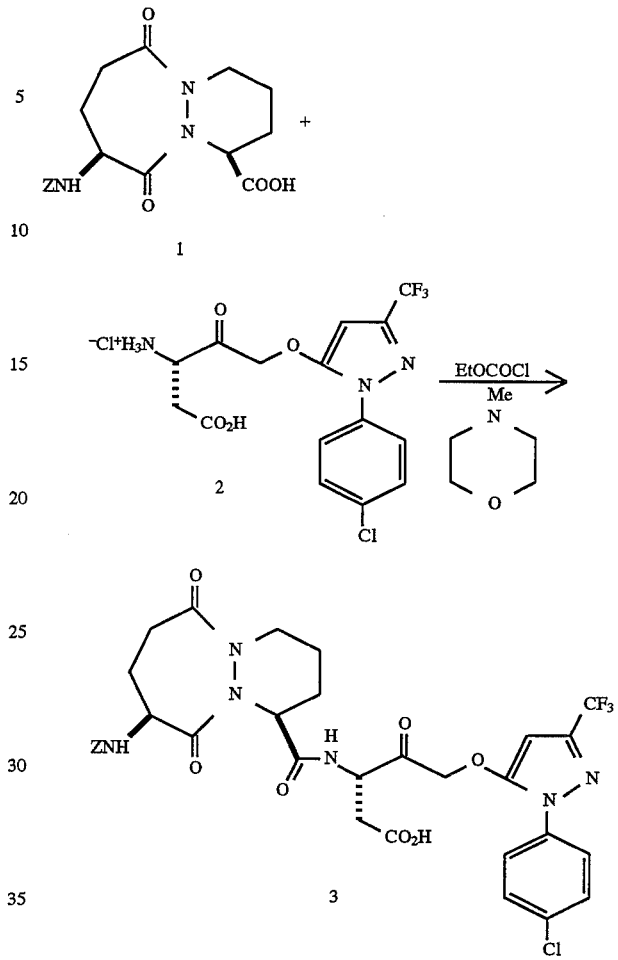

Part A: Compound 1 (1.25 g, 3.3 mmol) was dissolved in THF (20 mL). The solution was cooled to −15° C. and N-methylmorpholine (440 uL, 4 mmol) was added followed by ethyl chloroformate (342 uL, 3.6 mmol). After stirring for 15 min at −15° C., compound 2 (1.93 g, 4 mmol) was added along with N-methylmorpholine (440 uL, 4 mmol). The reaction was stirred 15 min at −15° C. and warmed to room temperature over 1 h. Ethyl acetate (200 mL) was added and the solution washed with water (100 mL) and saturated bicarbonate (50 mL) and dried over Na$_2$SO$_4$. Chromatography on silica gel eluting with a EtOAc-hexane gradient (10–70%) gave 1.5 g (58%) of the, coupled product 3.

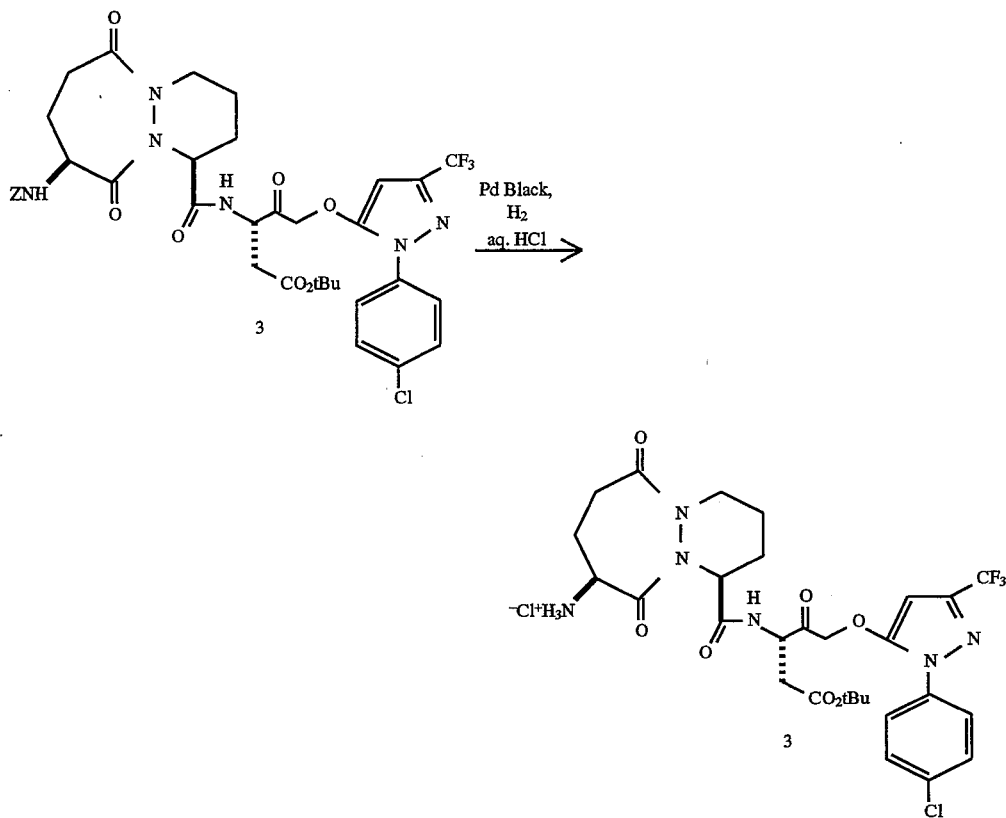
Part B: Compound 3 (1 g, 1.29 mmol) was dissolved in 200 mL of absolute ethanol. To this was added 6N HCl (2.1 mL, 2.58 mmol) and Pd black (100 mg). The solution was reduced on a Paar shaker (30 psi $H_2$) for 4 h. TLC (70% EtOAc/hexane) showed a $R_f$ drop from 0.75 to 0.00. The Pd was filtered off and solvent evaporated to give a quantative yield of the amine hydrochloride salt 4.
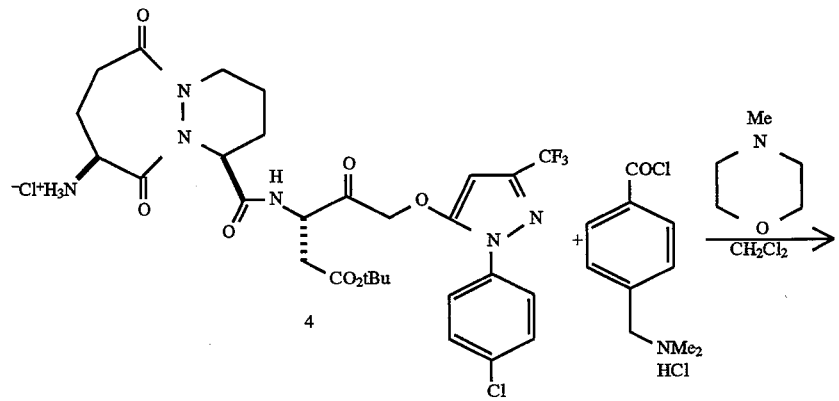

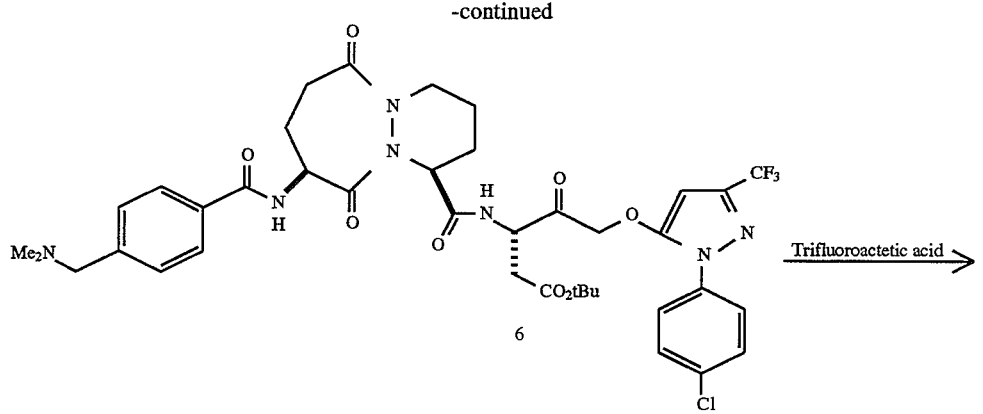

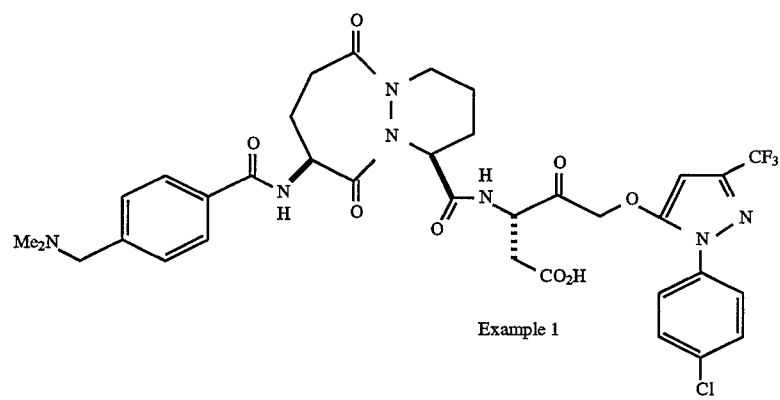

Example 1

Part C: To 4 (1.18 g, 1.68 mmol) in methylene chloride (40 mL at 0° C.) was added 5 (456 mg, 252 mmol). Next, N-methylmorpholine (920 uL, 8.4 mmol) was added along with dimethylaminopyridine (20 mg). The resulting mixture was stirred 30 min at 0° C. and 1 h at 25° C. The reaction mixture was washed with saturated bicarbonate. Purification by silica gel chromatography eluting with a MeOH/ methylene chloride gradient (2–10% MeOH) gave 1.5 g (76%) of the acylated product 6. This material was then treated with a 25% solution of TFA in $CH_2Cl_2$ to give the target compound using conditions described for the preparation of Formula 4.

Mass spectrum: 776 (M+H).

EXAMPLE 2

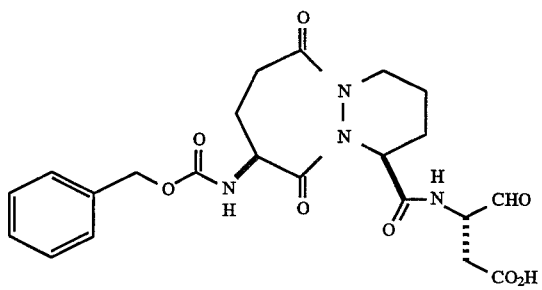

[9-Benzyloxycarbonylamino)octahydro-6,10-dioxo-6H-pyridazino[1,2a][1,2]diazepine-1-formoyl]-L-aspartic acid aldehyde

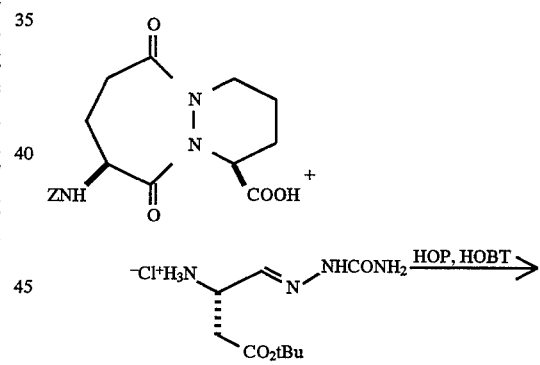

Part A: In a 200 mL round bottom flask were placed H-Asp(OtBu) semicarbazone 7 (269 mg, 1.17 mmol) diazepine acid 1 (504 mg, 1.35 mmol, 1.1 eq), benzotriazol-1-lyoxy-tris(dimethylamino)phosphonium 1 hexafluorophosphate (BOP) (672 mg, 1.52 mmol, 1.3 eq), HOBT (206 mg, 1.52 mmol, 1.3 eq) along with anhydrous DMF (60 mL). Then diisopropylethylamine (0.8 mL, 4.68 mmol, 4 eq) was added. The reaction mixture was stirred overnight at 25° C. and then the solvent was evaporated in vacuo. The residue was dissolved in EtOAc and washed with NaHCO$_3$ (saturated), H$_{2O}$ (3×), and brine. The organic layer was dried with NaSO$_4$, filtered and the solvent evaporated to yield white crystals (395 mg, 57%).

Mass spectrum: m/z 558 (M+H).

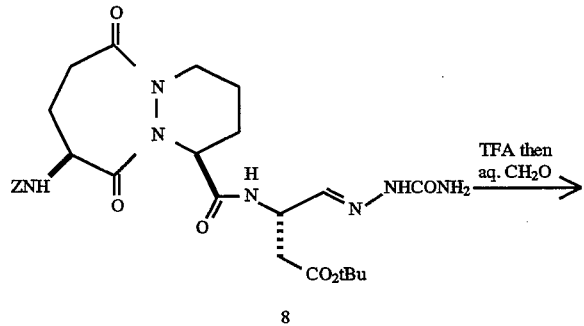

8

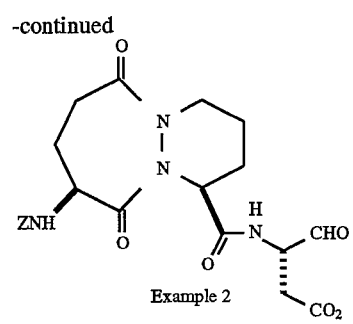

Example 2

Part B: In a round bottom flask, 2.0 mmol of 8 was added along with 70 mL of 25% trifluoroacetic acid in dichloromethane. After stirring for 2 h the solvents were removed in vacuo to give a semi-solid residue. The residue was taken up in 30 mL of MeOH to which was added 9 mL each glacial HOAc and of aq. 37% formaldehyde. The mixture was stirred for 2 h and water 50 mL was added. The MeOH was removed in vacuo and the aqueous solution diluted further with water and extracted with EtOAc. Further processing and purification by silica gel chromatography gave aldehyde Example 2 in ca. 50% overall yield from 1.

Mass spectrum: m/z 475 (M+H).

Using the methodology as described for the preparation of Example 1 and 2 and referencing Schemes 1,2 and 3, the following compounds were prepared:

EXAMPLE 3

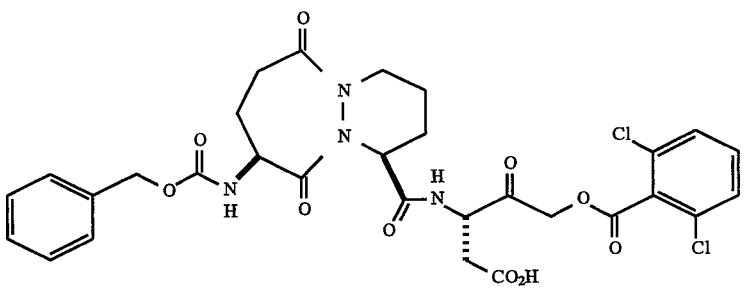

[9-Benzyloxycarbonylamino)octahydro-6,10-dioxo-6H-pyridazino[1,2a][1,2]diazepine-1-formoyl]-L-aspartic acid 2,6-dichlorobenzoyloxymethyl ketone mass spectrum: m/z 677 (M+H)

EXAMPLE 4

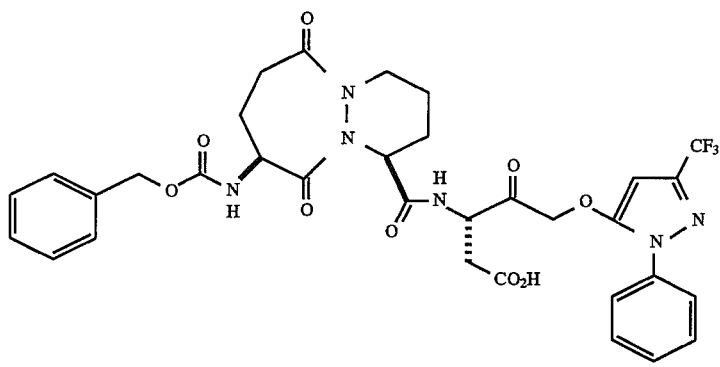

[9-Benzyloxycarbonylamino)octahydro-6,10-dioxo-6H-pyridazino[1,2a][1,2]diazepine-1-formoyl]-L-aspartic acid 5-(1-phenyl-3-trifluoromethyl)pyrazoloxymethyl ketone mass spectrum: m/z 715 (M+H)

EXAMPLE 5

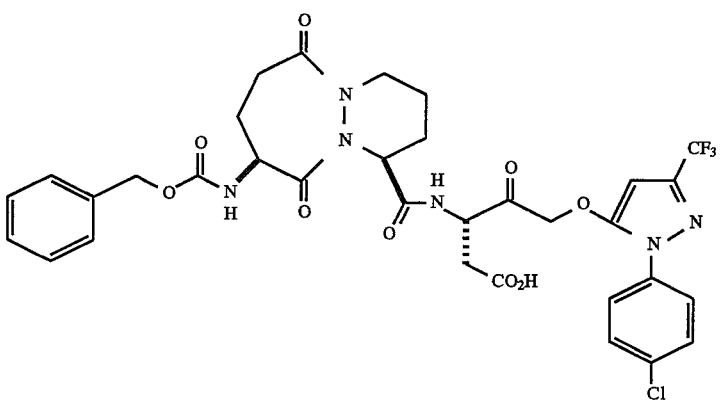

[9-Benzyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone mass spectrum: m/z 749 (M+H)

[9-Benzyroxycarbonylamino)octahydro-6,10-dioxo-6H-pyridazino[1,2a][1,2]diazepine-1-formoyl]-L-aspartic acid 5-(1-(2-pyridinyl)-3-trifluoromethyl)pyrazoloxymethyl ketone mass spectrum: m/z 716 (M+H)

EXAMPLE 6

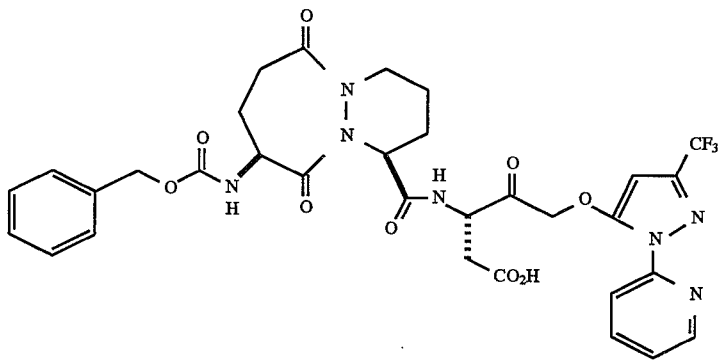

EXAMPLE 7

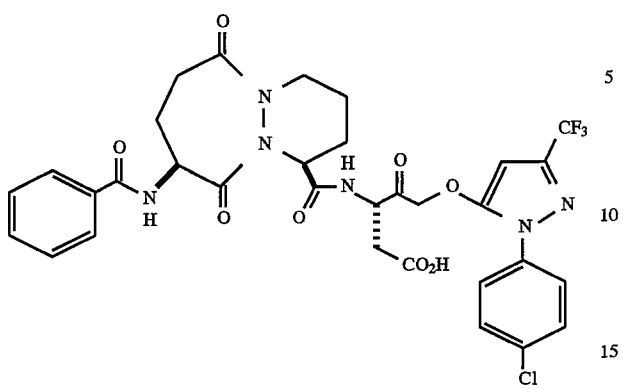

[9-Benzoylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone
mass spectrum: m/z 719=(M+H)

EXAMPLE 8

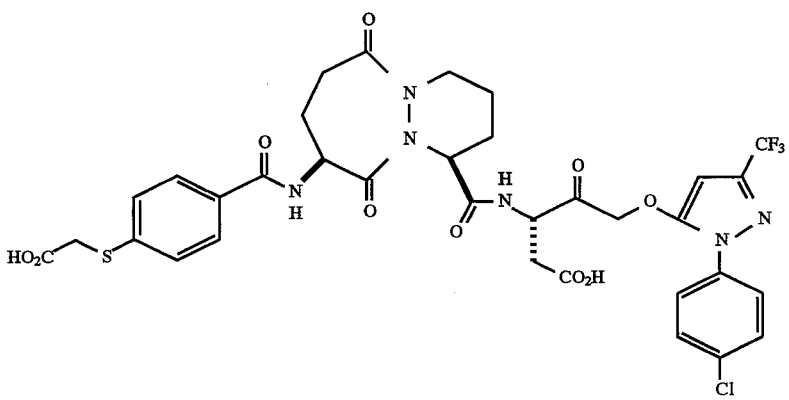

[9-(4-Carboxymethylthio)benzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone
mass spectrum: m/z 809 (M+H)

EXAMPLE 9

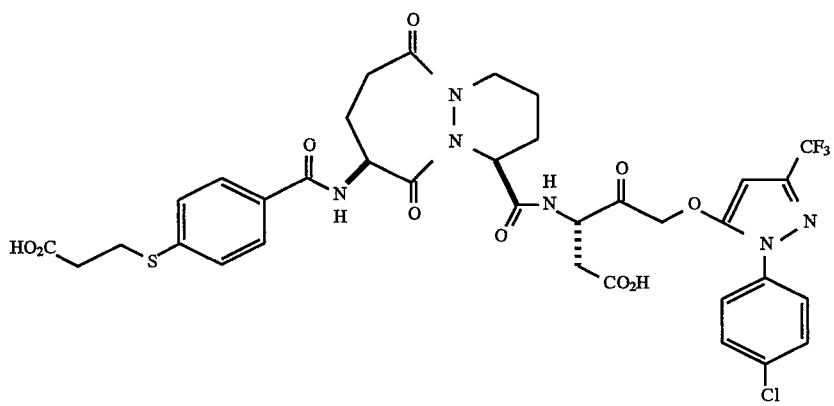

[9-(4-Carboxyethylthio)benzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone
mass spectrum: m/z 823 (M+H)

EXAMPLE 10

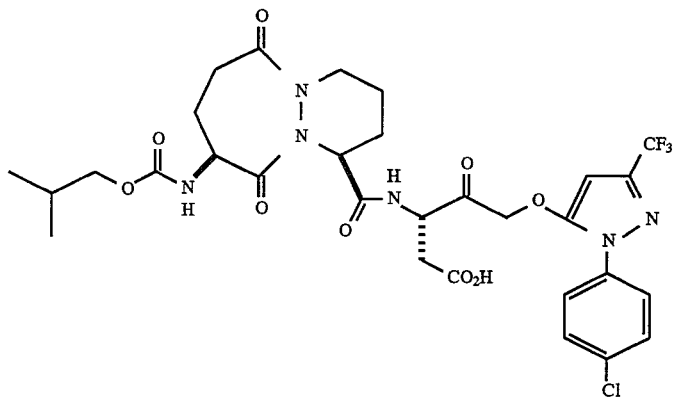

[9-Isobutyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone
mass spectrum: m/z 715 (M+H)

[9-(4-Carboxyethyl)benzoylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone
mass spectrum: m/z 791 (M+H)

EXAMPLE 11

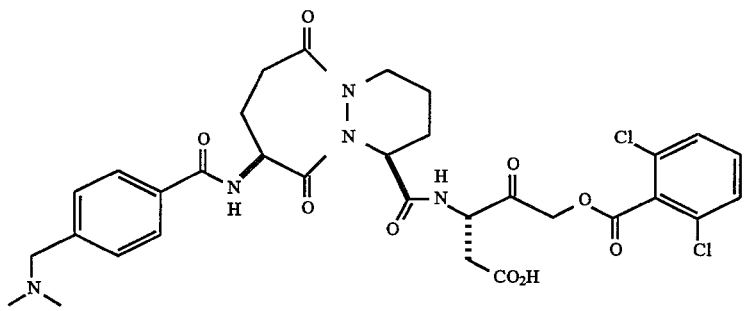

[9-(4-Dimethylaminomethyl)benzoylamino)octahydro-6,10-dioxo-6H-Pyridazino[1,2a][1,2]diazepine-1-formoyl]-L-aspartic acid 2,6-dichlorobenzoyloxymethyl ketone
mass spectrum: m/z 705 (M+H)

EXAMPLE 12

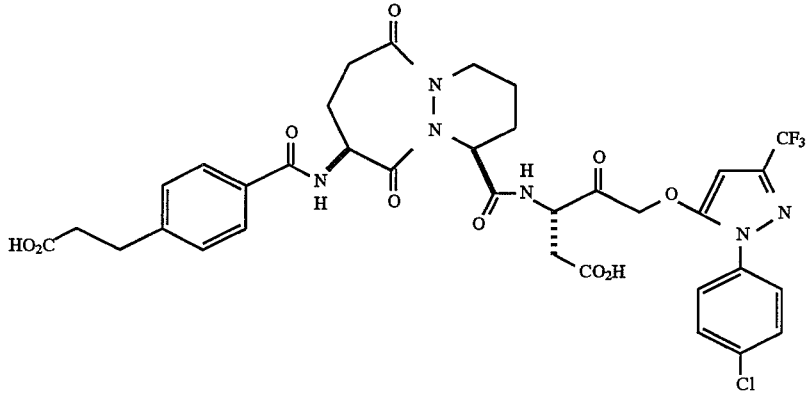

EXAMPLE 13

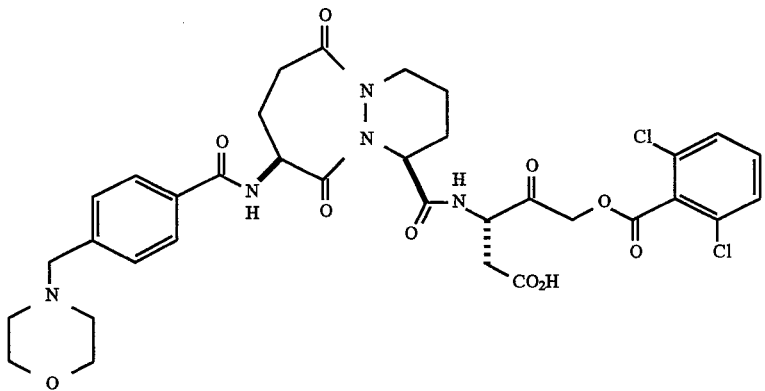

[9-(4-(N-Morpholinomethyl)benzoylamino)octahydro-6,10-dioxo-6H-pyridazino[1,2a][1,2]diazepine-1-formoyl]-L-aspartic acid 2,6-dichlorobenzoyloxymethyl ketone mass spectrum: m/z 746 (M+H)

EXAMPLE 14

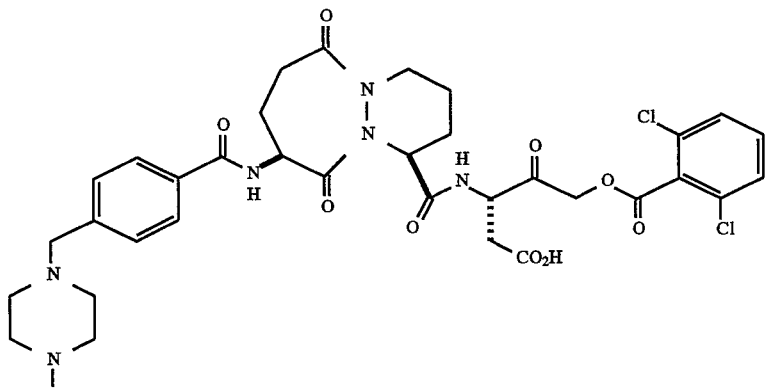

[9-(N-[4-(N-Methylpiperazino)methyl]benzoylamino)octahydro-6,10-dioxo-6H-pyridazino [1,2a][1,2]diazepine-1-formoyl]-L-aspartic acid 2,6-dichlorobenzoyloxymethyl ketone mass spectrum: m/z 759 (M+H)

[9-(4-(N-(2-Methyl)imidazolylmethyl)benzoylamino)octahydro-6,10-dioxo-6H-pyridazino[1,2a][1,2]diazepine-1-formoyl]-L-aspartic acid 2,6-dichlorobenzoyloxymethyl ketone mass spectrum: m/z 742 (M+H)

EXAMPLE 15

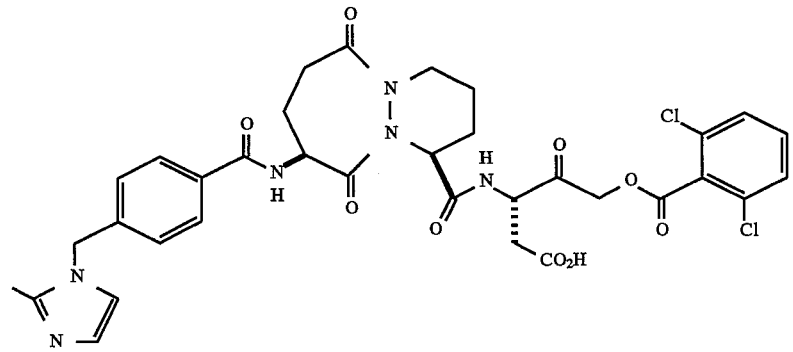

EXAMPLE 16

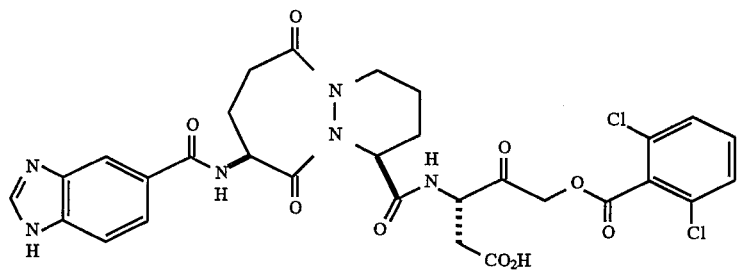

[9-(5-Benzimidazoylamino)octahydro-6,10-dioxo-6H-pyridazino[1,2a][1,2]diazepine-1-formoyl]-L-aspartic acid 2,6-dichlorobenzoyloxymethyl ketone mass spectrum: m/z 687 (M+H)

EXAMPLE 17

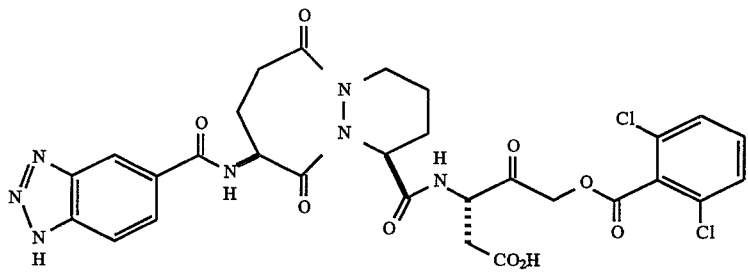

[9-(5-Bentriazoylamino)octahydro-6,10-dioxo-6H-pyridazino[1,2a][1,2]diazepine-1-formoyl]-L-aspartic acid 2,6-dichlorobenzoyloxymethyl ketone mass spectrum: m/z 688 (M+H)

EXAMPLE 18

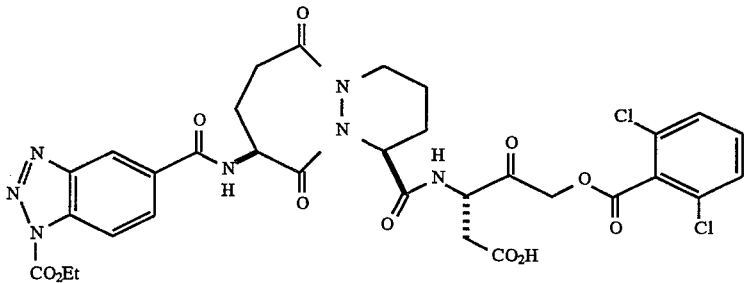

[9-(N-Carboethoxy-5-bentriazoylamino)octahydro-6,10-dioxo-6H-pyridazino[1,2a][1,2]diazepine-1-formoyl]-L-aspartic acid 2,6-dichlorobenzoyloxymethyl ketone mass spectrum: m/z 760 (M+H)

EXAMPLE 19

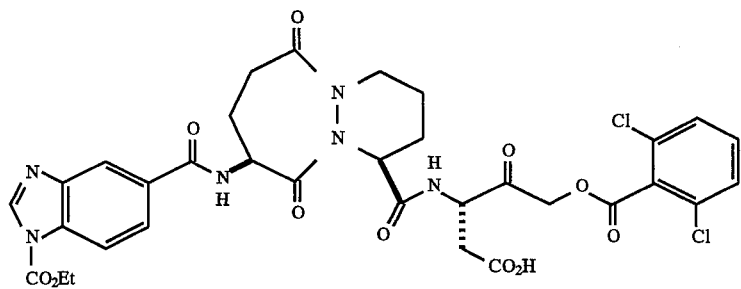

[9-(N-Carboethoxy-5-benzimidazoylamino)octahydro-6,
10-dioxo-6H-pyridazino[1,2a][1,2]diazepine-1-formoyl]-L-
aspartic acid 2,6-dichlorobenzoyloxymethyl ketone mass spectrum: m/z 759 (M+H)

EXAMPLE 20

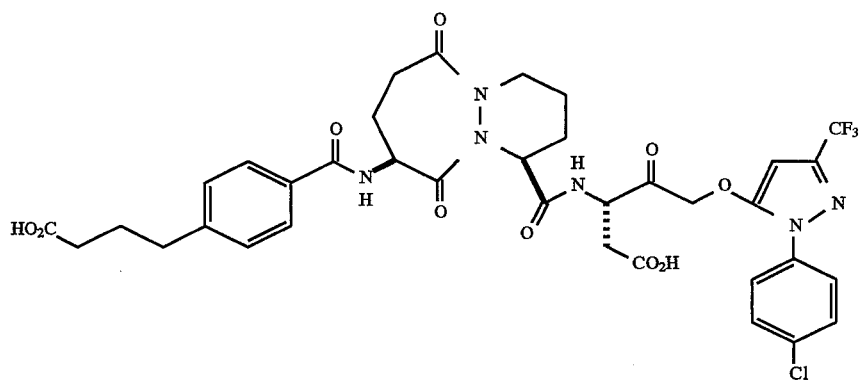

[9-(4-Carboxypropyl)benzoylamino)octahydro-6,10-dioxo-
6H-pyridazino[1,2a][1,2]diazepine-1-formoyl]-L-aspartic
acid 5-(1-(4-chlorophenyl)-3-trifluoro-5 methyl)
pyrazoloxymethyl ketone mass spectrum: m/z 805 (M+H)

EXAMPLE 21

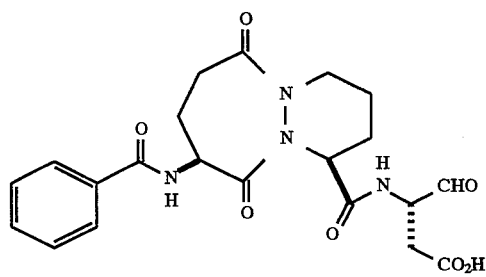

[9-Benzoylamino)octahydro-6,10-dioxo-6H-pyridazino[1,
2a][1,2]diazepine-1-formoyl]-L-aspartic acid aldehyde mass spectrum: m/z 446 (M+H)

EXAMPLE 22

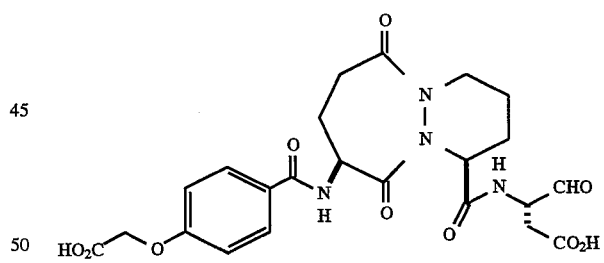

[9-(4-Carboxymethoxy)benzoylamino)octahydro-6,10-
dioxo-6H-pyridazino[1,2a][1,2]diazepine-1-formoyl]-L-
aspartic acid aldehyde mass spectrum: m/z 519 (M+H)

EXAMPLE 23

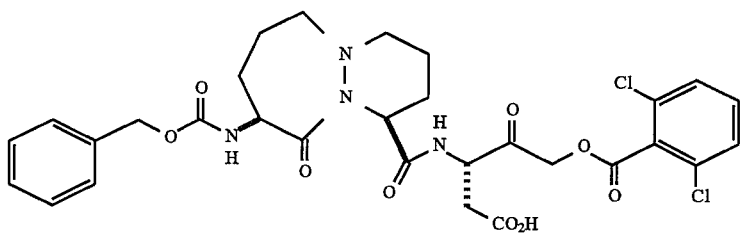

[9-Benzyloxycarbonylamino)octahydro-10-oxo-6H-pyridazino[1,2a][1,2]diazepine-1-formoyl]-L-aspartic acid 2,6-dichlorobenzoyloxymethyl ketone mass spectrum: m/z 663 (M+H)

EXAMPLE 24

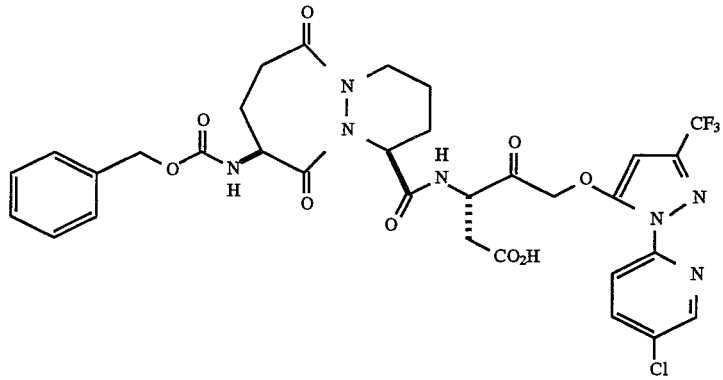

[9-Benzyloxycarbonylamino)octahydro-6,10-dioxo-6H-pyridazino[1,2a][1,2]diazepine-1-formoyl]-L-aspartic acid 5-(1-(4-chloro-2-pyridinyl)-3-trifluoromethyl) pyrazoloxymethyl ketone mass spectrum: m/z 750 (M+H)

EXAMPLE 25

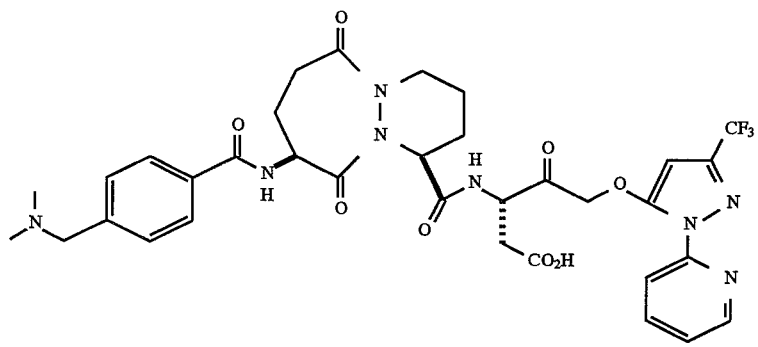

[9-(4-Dimethylaminomethyl)benzoylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone mass spectrum: m/z 743 (M+H)

EXAMPLE 26

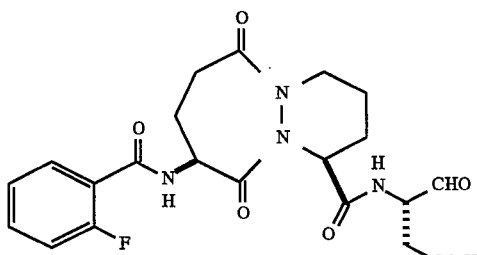

[9-(2-Fluorobenzoylamino)octahydro-6,10-dioxo-6H-pyridazino[1,2a][1,2]diazepine-1-formoyl]-L-aspartic acid aldehyde mass spectrum m/z 463 (M+H)

EXAMPLE 27

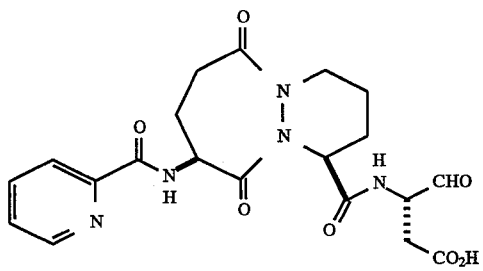

[9-(2-Pyridinoylamino)octahydro-6,10-dioxo-6H-pyridazino[1,2a][1,2]diazepine-1-formoyl]-L-aspartic acid aldehyde mass spectrum m/z 446 (M+H)

EXAMPLE 28

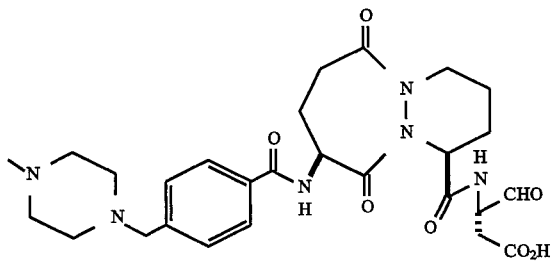

[9-(N-[4-Methylpiperazino)methyl]benzoylamino)octahydro-6,10-dioxo-6H-pyridazino[1,2a][1,2]diazepine-1-formoyl]-L-aspartic acid aldehyde mass spectrum m/z 557 (M+H)

In Vitro Assay

Second order rates of inactivation were obtained by using the enzyme assay described in Dolle, R. E.; et al., *J. Med Chem.* (1994), 37, 563. Note that aldehydes of Examples 2, 21, 22 and 26–28 are reversible inhibitors and display slow binding kinetics. In the case of these reversible inhibitors, the in vitro assay was modified to obtain the reversible $K_i^*$ as follows:

$K_i^*$ values for reversible inhibitors were determined by preincubating ICE with various concentrations of inhibitor in 10 mM HEPES (a common laboratory buffer; pH 7.5), 25% glycerol, 1 mM dithiothreitol for 30 minutes at 37 °C. in a polystyrene 96-well plate. Remaining ICE activity was measured by adding 10 uM Succinyl-Tyrosine-Valine-Alanine-Aspartic acid-amino methylcoumarin (Bachem Bioscience, Inc.) and monitoring the increase in fluorescence at 37° C. using a Fluoroskan II fluorescence plate reader. The $K_i^*$ was calculated from a plat of 1/v versus I as described previously (Morrison, J. F. and Cleland, W. W. (1983) Biochemistry 22, 5507–5513.

The compounds of example 1, 3–20, and 23–25 posses IL-1β protease inhibition ($k_{obs}/[I]$=>10,000 $M^{-1}$ $s^{-1}$) while compounds of examples 2, 21,22 and 26–28 also possess IL-1β protease inhibition ($K_i^*$=<10 μM).

In Vivo Assay

In vivo inhibition ($IC_{50}$) was determined as follows:

Human monocytes were isolated from heparinized leukopheresis units obtained through Biological Specialty Corporation (Lansdale, Pa.). Monocytes were purified by Ficoll-Hupaque (Pharmacia Fine Chemicals, Piscataway, N.J.) gradient centrifugation and more than 95% pure monocyte populations obtained by centrifugal elutriation. The assay was performed on duplicate samples of freshly isolated human monocytes, cultured in suspension at 37° C. and rotated gently in conical bottom polypropylene tubes (Sardstedt Inc., Princeton, N.J.). Human monocytes at a concentration of 5×10⁶ cells/mL were resuspended in 1 mL of RPMI 1640 (a common tissue buffer from M. A. Bioproducts, Walkersville, Md.) containing 1% fetal calf serum (FCS) (HyClone, Logan, Utah) and 50 μg/mL gentamycin (Gibco, Grand Island, N.Y.). The cells were treated either with a compound of the invention (i.e. test compound) or with a non-inhibitor (control compound, typically 0.03% DMSO) for 15 minutes and then activated with 0.01% fixed *Staphylococcus aureus* (The Enzyme Center, Malden, Mass.) for 1 hour. The cells were then centrifuged and resuspended in 1 mL of cysteine, methionine-free RPMI media containing 1% dialyzed FCS (Hyclone). The cells were pretreated with a test compound or control compound for 15 minutes after which 0.01% fixed *S. aureus* plus 100 μCi Tran 35-S label (ICN, Irvine, Calif.) was added and the cells incubated at 37° C. for 1 hour. After incubation, cells were centrifuged, washed once in phosphate buffer saline and resuspended in 1 mL RPMI containing 1% fetal calf serum. The cells were again pretreated with a test or control compound for 15 minutes and then 0.01% *S. aureus* for 2 hours. At the end of the incubation, cells were centrifuged and supernates saved for immunoprecipitation. Cells were washed once in phosphate buffer saline and then lysed in RIPA, a continuous cell media buffer containing 2 mM phenylmethylsulfonyl fluoride, 10 mM iodoacetate, 1 μg/mL pepstatin A, 1 μg/mL leupeptin and 0.5 TIU aprotinin.

For the immunoprecipitations, an equal volume of 1% dry milk in RIPA buffer plus 50 μL of resuspended protein A sepharose CL-4B (Pharmacia, Piscataway, N.Y.) was added to supernates and 1 mL of 4% dry milk containing protein A sepharose CL-4B to cell lysates and samples rotated for 30 minutes at 4° C. Beads were then centrifuged down, samples transferred to fresh tubes and incubated overnight with 40 μg rabbit anti-human IL-1β polyclonal antibody (Genzyme, Cambridge, Mass.). The IL-1β proteins were then precipitated with 70 μL protein A sepharose, resuspended in 60 μL SDS sample buffer and run on 15% SGD-PAGE gels. Autoradiography was performed on dried gels and the amount of radioactivity (counts per minute, cpm) quantitated using a Betascope 603 analyzer.

Data Analysis

In the monocyte pulse chase assay, each test parameter was run in duplicate. Data was collected from the Beta Scope using a personal computer, then transferred to the VAX system for calculation of mean cpm and standard deviation of the mean. When test compounds were evaluated, the percent inhibition of release of mature IL-1β was calculated as follows:

100×[1−(cells treated with stimuli+test compound−unstimulated cells)/(cells treated with stimuli+control compound−unstimulated cells)]

These % inhibition values were then used to calculate $IC_{50}$ value for each compound. Since the human monocyte pulse chase assay uses primary cells from different donors, each test compound was run in 2-3 separate experiments, using monocytes from 2-3 different donors.

For examples 1-25, the in vivo $IC_{50}$'s were <10 µM.

We claim:

1. A compound of the formula (A) or a pharmaceutically acceptable salt thereof:

wherein:

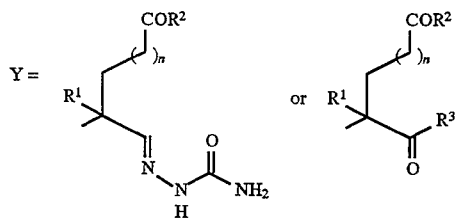

and when $R^2$=OH then Y may also be

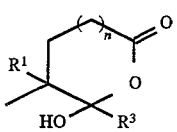

wherein n=0,1;

$R^1$=H or deuterium;

$R^2$=$OR^4$ or NHOH;

$R^4$=H, alkyl, cycloalkyl or aralkyl;

$R^3$=H, $(CR^8R^9)_{0-6}CF_3$, $(CR^8R^9)_{0-6}CF_2CF_3$, $(CR^8R^9)_{0-6}COOR^5$, $(CR^8R^9)_{0-6}CONR^6R^7$, $CF_2(CR^8R^9)_{0-6}$aryl, $CF_2(CR^8R^9)_{0-6}$heteroaryl, $CF_2(CR^8R^9)_{0-6}$alkyl, $CHN_2$, $CH_2R^{10}$ or $COR^5$;

wherein $R^5$=H, alkyl, cycloalkyl, aryl, aralkyl, heteroaryl or heteroaralkyl;

$R^6$ and $R^7$ are independently selected from the group consisting of H, alkyl, cycloalkyl, aryl, aralkyl, heteroaryl and heteroaralkyl and where $R^6$ and $R^7$ are taken together may be a 3-,4-,5-,6- or 7-membered carbocyclic ring;

$R^8$ and $R^9$ are independently H, or alkyl;

$R^{10}$=alkyl, aryl, aralkyl, heteroaryl, heteroaralkyl, H, halo, $SR^5$, $SR^5R^6$, $O(CO)_{0-1}$aryl, $O(CO)_{0-1}$heteroaryl, OP(O)$R^{11}R^{12}$,

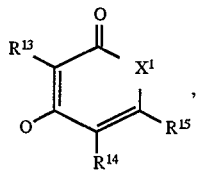

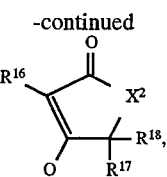

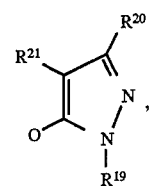

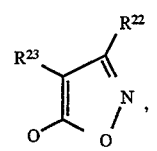

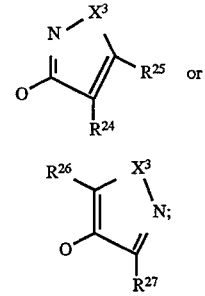

$R^{11}$ and $R^{12}$ are selected from the group consisting of H, OH, alkyl, cycloalkyl, aryl, aralkyl, heteroaryl, heteroaralkyl, alkoxy, aroxy, aralkyloxy, heteroaroxy and heteroaralkyloxy;

$R^{13}$=H, alkyl, aryl or aralkyl;

$R^{14}$ and $R^{15}$ are selected from the group consisting of H, alkyl and aryl, or when taken together $R^{14}$ and $R^{15}$ is an aryl ring;

$X^1$=O, S or $NR^{28}$ where $R^{28}$=H, alkyl, aryl, aralkyl, heteroaryl or heteroaralkyl;

$R^{16}$=H, Cl, alkyl or $(CR^8R^9)_{0-6}$-aryl;

$R^{17}$ and $R^{18}$ are independently H or alkyl;

$X^2$=$CH_2$, O or $NR^{28}$;

$R^{19}$=H, alkyl, cycloalkyl, alkylcycloalkyl, aryl, aralkyl, heteroaryl or heteroaralkyl;

$R^{20}$=H, alkyl, $CF_3$, $CF_2CF_3$, $COOR^5$, $CONR^6R^7$, cycloalkyl, alkylcycloalkyl, aryl, aralkyl, heteroaralkyl or heteroaryl;

$R^{22}$, $R^{23}$, $R^{24}$, $R^{25}$, $R^{26}$, and $R^{27}$ are selected from the group consisting of H, alkyl, cycloalkyl, alkylcycloalkyl, aryl, aralkyl, heteroaryl, heteroaralkyl and $R^{29}$; and where $R^{24}$ and $R^{25}$ when taken together may be aryl or heteroaryl;

$X^3$=O or S;

$R^{29}$=F, Cl, $CF_3$, $CF_2CF_3$, $(CF_2)_{0-3}$—H, $COOR^5$ or $CONR^{30}R^{31}$, where $R^{30}$ and $R^{31}$ are selected from the group consisting of $R^6$, $R^7$,

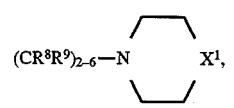

-continued

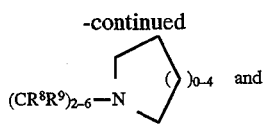

Z =

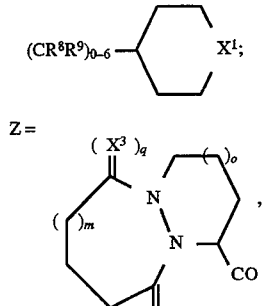

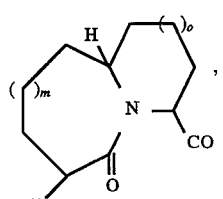

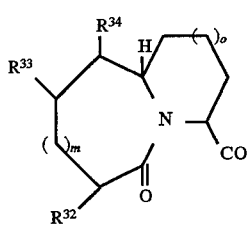

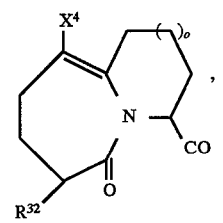

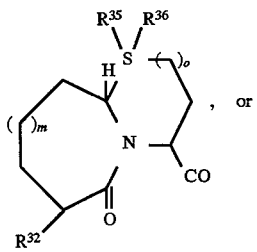

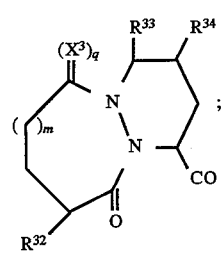

wherein
q=0 or 1;
m=0, 1, 2 or 3;

m=0, 1, 2 or 3;
o=0, 1 or 2;
$X^4$=H or alkylthio;

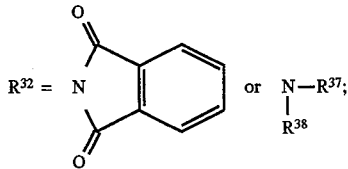

$R^{33}$ and $R^{34}$ are selected from the group consisting of alkyl, aryl or when taken together, $R^{33}$ and $R^{34}$ are aryl, heteroaryl, or a double bond;

$R^{35}$ and $R^{36}$ are an oxygen atom;

$R^{37}$=H or alkyl;

$R^{38}$ is selected from the group consisting of H, alkyl, aryl, aralky, heteroaryl, heteroaralkyl, $R^{40}$—$SO_2$, $R^{41}$—CO, $R^{50}O$—CO and $R^{51}NR^5$—CO;

wherein $R^{40}$=$R^5$ or $HNR^5$;

$R^{41}$=alkenyl, aralkenyl, heteroaralkenyl, alkynyl, aralkynyl, heteroaralkynyl, $R^{42}$—$OCOR^5$, $R^{43}$—$COR^5$, $R^{42}$—$NR^{47}C(=NR^6)R^5$, $R^{42}$—$NR^{47}(=NR^6)NR^5$, $R^{42}$—$SR^5$, $R^{42}$—$S(CR^8R^9)_{1-6}COOR^{47}$, $R^{42}$—$S(CR^8R^9)_{1-6}COONR^{47}R^{48}$, $R^{42}$—$OR^5$, $R^{42}$—$O(CR^8R^9)_{1-6}COOR^{47}$, $R^{42}$—$O(CR^8R^9)_{1-6}COONR^{47}R^{48}$, $R^{42}$—$NR^5SO_2R^6$, $R^{43}$—$R^{44}$, $R^{43}$—$R^{45}$, $R^{43}$—$R^{46}$, $R^{43}$—$NR^{47}R^{48}$, $R^{42}$—OH or $R^{43}$—$CF_3$;

wherein $R^{42}$=$(CR^8R^9)_{1-7}$ and $R^{43}$=$(CR^8R^9)_{0-6}$;

R44=H, alkyl, —$(CH_2)0$-4-cycloalkyl,

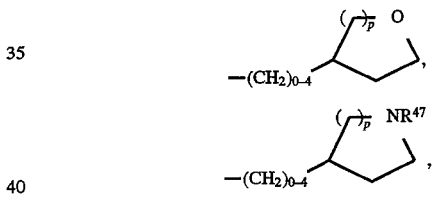

aryl, heteroaryl, aralkyl, heteroaralkyl or —$(CH_2)_{2-6}$—$R^{49}$;
wherein p=1–4;

$R^{49}$=alkoxy, $CH_2F$, $CHF_2$, $CF_3$, $CF_2CF_3$, OH, $COOR^{47}$, $CONR^{47}R^{48}$, or $NR^{47}R^{48}$;

wherein $R^{48}$ is H, alkyl, aryl, aralkyl, heteroaryl, heteroaralkyl, $CH_2CH_2O$-alkyl or C(O)—$R^{49}$;

$R^{47}$ is H, alkyl, cycloalkyl, aryl, aralkyl, heteroaryl or heteroaralkyl;

and when $R^{47}$ and $R^{48}$ are taken together, they can equal a five, six or seven membered ring of the type:

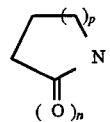

where p=1–4 and n=0–1;

$R^{49}$ is alkyl, aryl, aralkyl, heteroaryl or heteroaralkyl;

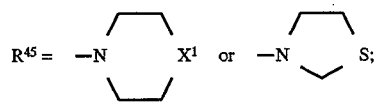

-continued

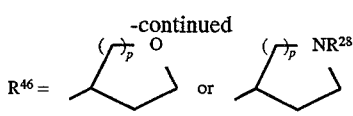

where p=1–4;

$R^{50}$ and $R^{51}$ are independently selected from the group consisting of alkyl, $R^{43}$-cycloalkyl, aryl, aralkyl, heteroaryl, heteroaralkyl, $R^{42}$-alkenyl, $R^{42}$-heteroaralkenyl, $R^{42}$-alkynyl, $R^{42}$-aralkynyl, $R^{42}$-heteroaralkynyl, $R^{43}$—$R^{46}$, $R^{42}$—$R^{49}$, $R^{52}$—$R^{45}$, $R^{42}$—$COOR^{47}$, $R^{42}$—$CONR^{47}R^{48}$, $R^{52}$—$OCOR^{5}$, $R^{52}$—$COR^{5}$, $R^{52}$—$NR^{47}C(=NR^{6})R^{5}$, $R^{52}$—$NR^{47}(=NR^{6})NR^{5}$, $R^{52}$—$SR^{5}$, $R^{52}$—$S(CR^{8}R^{9})_{1-6}COOR^{47}$, $R^{52}$—$S(CR^{8}R^{9})_{1-6}COONR^{47}R^{48}$, $R^{52}$—$OR^{5}$, $R^{52}$—$O(CR^{8}R^{9})_{1-6}COOR^{47}$, $R^{52}$—$O(CR^{8}R^{9})_{1-6}COONR^{47}R^{48}$, $R^{52}$—$NR^{5}SO_{2}R^{6}$, $R^{52}$—$R^{44}$ and $R^{52}$—$NR^{47}R^{48}$, where $R^{52}=(CR^{8}R^{9})_{2-6}$.

2. The compound according to claim 1 wherein:
$R^{2}=OR^{4}$;
$R^{3}=H$, $COR^{5}$, $COOR^{5}$, $CONR^{6}R^{7}$, $CF_{2}(CR^{8}R^{9})_{0-6}$aryl, $CF2(CR^{8}R^{9})_{0-6}$heteroaryl, $CF_{2}(CR^{8}R^{9})_{0-6}$alkyl, $CHN_{2}$ or $CH_{2}R^{10}$.

3. The compound according to claim 2 wherein:
$R^{10}$ is =alkyl, aryl, aralkyl, heteroaryl, heteroaralkyl, halo, $O(CO)_{0-1}$ aryl, $O(CO)_{0-1}$ heteroaryl, $OP(O)R^{11}R^{12}$,

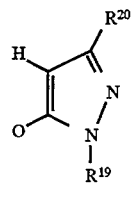

or

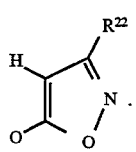

4. The compound according to claim 3 wherein:
$R^{10}$=halo, $O(CO)_{0-1}$ aryl, OCO-heteroaryl, $OP(O)R^{10}R^{12}$,

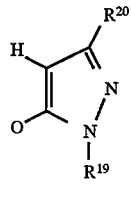

or

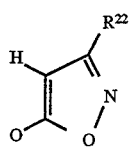

where $R^{11}$ and $R^{12}$ are independently alkyl, aralkyl or aryl; $R^{19}$=aryl; $R^{20}$=alkyl, $CF_{3}$, $CF_{2}CF_{3}$, $COOR^{8}$ or $CONR^{6}R^{7}$; $R^{22}$=aryl, aralkyl, heteroaryl or heteroaralkyl.

5. The compound according to claim 1 wherein:

Z=

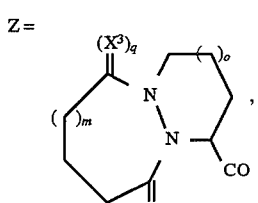

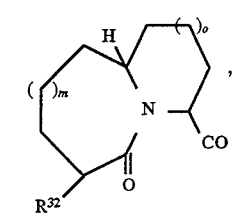

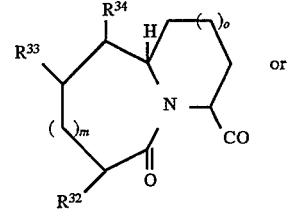

or

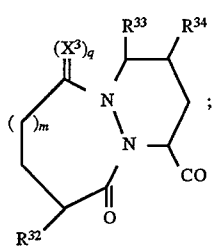

where $X^{3}=O$; q=0 or 1; m=1 or 2; O=1; $R^{33}$ and $R^{34}$ when taken together may be aryl or a double bond and where $R^{37}=H$.

6. The compound according to claim 2 wherein:

Z=

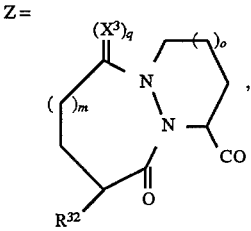

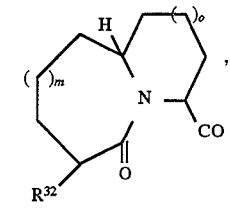

-continued

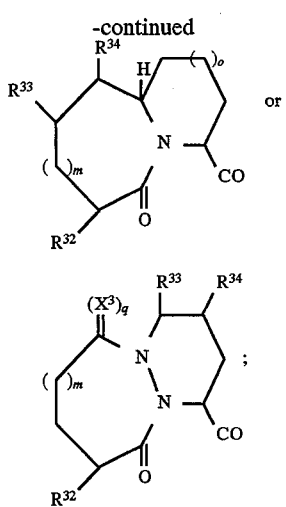

where $X^3$=O; q=0 or 1; m=1 or 2; O=1; $R^{33}$ and $R^{34}$ when taken together may be aryl or a double bond and where $R^{37}$=H.

7. The compound according to claim 3 wherein:

Z=

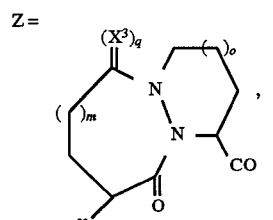

,

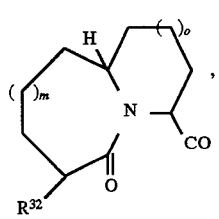

,

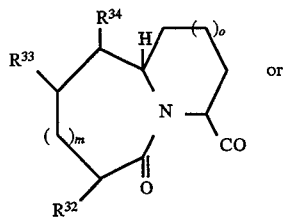

or

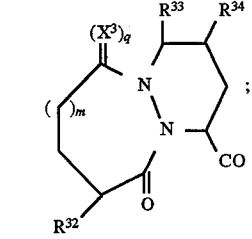

;

where $X^3$=O; q=0 or 1; m=1 or 2; O=1; $R^{33}$ and $R^{34}$ when taken together may be aryl or a double bond and where $R^{37}$=H.

8. The compound according to claim 4 wherein:

Z=

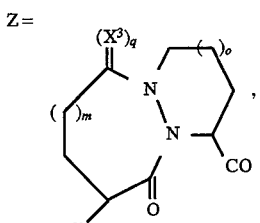

,

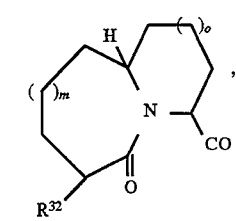

,

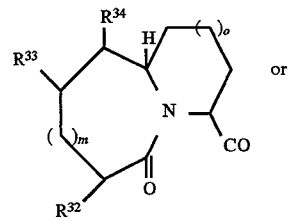

or

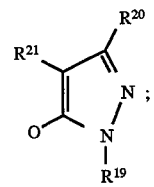

;

where $X^3$=O; q=0 or 1; m=1 or 2; O=1; $R^{33}$ and $R^{34}$ when taken together may be aryl or a double bond and where $R^{37}$=H.

9. The compound according to claim 2 wherein:
$R^4$=H or alkyl;
$R^3$=H or $CH_2R^{10}$;
$R^{10}$=halo, OCO-aryl or

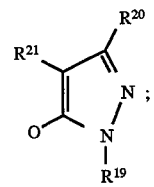

;

$R^{19}$=aryl; $R^{20}$=alkyl, $CF_3$ or $CF_2CF_3$; $R^{21}$=H;

Z=

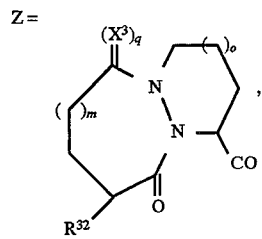

,

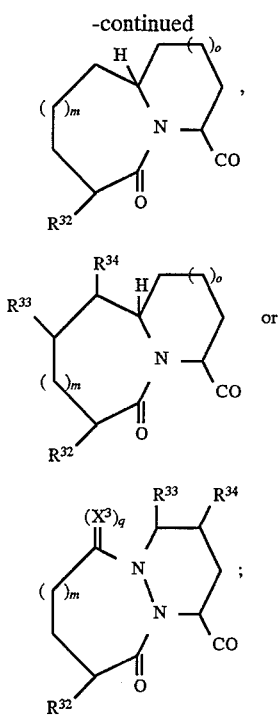

where $X^3=O$; $q=0$ or 1; $m=1$ or 2; $O=1$; $R^{33}$ and $R^{34}$ when taken together may be aryl or a double bond and where $R^{37}=H$.

10. The compound according to claim 9 wherein:

$Z =$

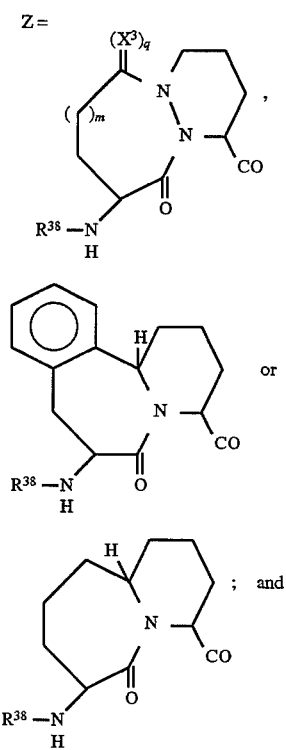

$m=1$ or 2; $X^3=O$; and $q=0$ or 1.

11. The compound according to claim 9 wherein:

$Z =$

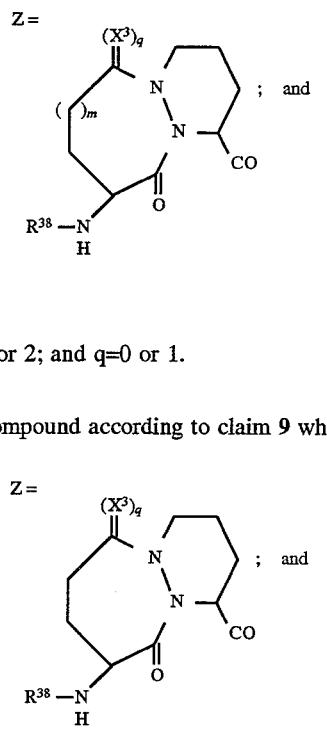

$X^3=O$; $m=1$ or 2; and $q=0$ or 1.

12. The compound according to claim 9 wherein:

$Z =$

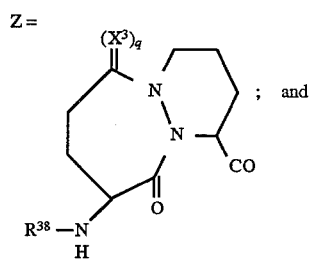

$X^3=$; $m=1$ or 2; and $q=0$ or 1.

13. The compound according to claim 10 wherein:

$Y =$

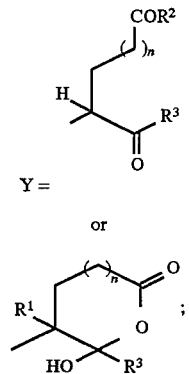

$R^4=H$ or alkyl; $n=0$; $R^3=H$, $CH_2$-halo, $CH_2$—OCO-aryl, or

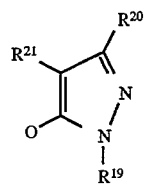

wherein $R^{21}=H$ or alkyl.

14. The compound according to claim 13 wherein:

Z =

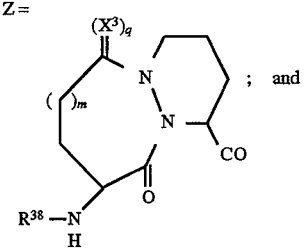

and

X³=O; m=1 or 2; and q=0 or 1.

15. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound selected from the group consisting of:

[9-(Benzyloxycarbonylamino)octahydro-6,10-dioxo-6H-pyridazino[1,2a][1,2]diazepine-1-formoyl]-L-aspartic acid aldehyde;

[9-Benzoylamino)octahydro-6,10-dioxo-6H-pyridazino[1,2a][1,2]diazepine-1-formoyl]-L-aspartic acid aldehyde;

[9-(4-Carboxymethoxybenzoylamino)octahydro-6,10-dioxo-6H-pyridazino[1,2a][1,2]diazepine-1-formoyl]-L-aspartic acid aldehyde;

[9-(2-Fluorobenzoylamino)octahydro-6,10-dioxo-6H-pyridazino[1,2a][1,2]diazepine-1-formoyl]-L-aspartic acid aldehyde;

[9-(2-Pyridinoylamino)octahydro-6,10-dioxo-6H-pyridazino[1,2a][1,2]diazepine-1-formoyl]-L-aspartic acid aldehyde; and

[9-(N-4-Methylpiperazinomethylbenzoylamino)octahydro-6,10-dioxo-6H-pyridazino[1,2a][1,2]diazepine-1-formoyl]-L-aspartic acid aldehyde.

16. The compound according to claim 1 selected from the group consisting of:

[9-(Benzyloxycarbonylamino)octahydro-6,10-dioxo-6H-pyridazino[1,2a][1,2]diazepine-1-formoyl]-L-aspartic acid 2,6-dichlorobenzoyloxymethyl ketone;

[9-(4-Dimethylaminomethylbenzoylamino)octahydro-6,10-dioxo-6H-pyridazino[1,2a][1,2]diazepine-1-formoyl]-L-aspartic acid 2,6-dichlorobenzoyloxymethyl ketone;

[9-(N-[4-Methylpiperazinomethyl]benzoylamino)octahydro-6,10-dioxo-6H-pyridazino[1,2a][1,2]diazepine-1-formoyl]-L-aspartic acid 2,6-dichlorobenzoyloxymethyl ketone;

[9-(4-(N-Methylpiperazinylmethyl)benzoylamino)octahydro-6,10-dioxo-6H-pyridazino[1,2a][1,2]diazepine-1-formoyl]-L-aspartic acid 2,6-dichlorobenzoyl-oxymethyl ketone; and

[9-(4-(N-(2-Methyl)imidazolylmethyl)benzoylamino)octahydro-6,10-dioxo-6H-pyridazino [1,2a][1,2]diazepine-1-formoyl]-L-aspartic acid 2,6-dichlorobenzoyloxymethyl ketone.

17. The compound according to claim 1 selected from the group consisting of:

[9-(5-Benzimidazoylamino)octahydro-6,10-dioxo-6H-pyridazino[1,2a][1,2]diazepine-1-formoyl]-L-aspartic acid 2,6-dichlorobenzoyloxymethyl ketone;

[9-(5-Bentriazoylamino)octahydro-6,10-dioxo-6H-pyridazino[1,2a][1,2]diazepine-1-formoyl]-L-aspartic acid 2,6-dichlorobenzoyloxymethyl ketone;

[9-(N-Carboethoxy-5-bentriazoylamino)octahydro-6,10-dioxo-6H-pyridazino[1,2a][1,2]diazepine-1-formoyl]-L-aspartic acid 2,6-dichlorobenzoyloxymethyl ketone;

[9-(N-Carboethoxy-5-benzimidazoylamino)octahydro-6,10-dioxo-6H-pyridazino[1,2a][1,2]diazepine-1-formoyl]-L-aspartic acid 2,6-dichlorobenzoyloxymethyl ketone; and

[9-(Benzyloxycarbonylamino)octahydro-10-oxo-6H-pyridazino[1,2a][1,2]diazepine-1-formoyl]-L-aspartic acid 2,6-dichlorobenzoyloxymethyl ketone.

18. The compound according to claim 1 selected from the group consisting of:

[9-(4-Dimethylaminomethylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-phenyl-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone; and

[9-(Benzoylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone.

19. The compound according to claim 1 selected from the group consisting of:

[9-(4-Carboxymethylthiobenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(4-Carboxyethylthiobenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Isobutyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(4-Carboxyethylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl)-pyrazoloxymethyl ketone;

[9-(4-Carboxypropylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(4-chloro-2-pyridinyl)-3-trifluoromethyl) pyrazoloxymethyl ketone; and

[9-(4-Dimethylaminomethylbenzoylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone.

20. The compound according to claim 1 selected from the group consisting of:

[9-(Benzyloxycarbonylamino)octahydro-6,10-dioxo-6H-pyridazino[1,2a][1,2]diazepine-1-formoyl]-L-aspartic acid aldehyde;

[9-(Benzoylamino)octahydro-6,10-dioxo-6H-pyridazino[1,2a][1,2]diazepine-1-formoyl]-L-aspartic acid aldehyde;

[9-(4-Carboxymethoxybenzoylamino)octahydro-6,10-dioxo-6H-pyridazino[1,2a][1,2]diazepine-1-formoyl]-L-aspartic acid aldehyde;

[9-(2-Fluorobenzoylamino)octahydro-6,10-dioxo-6H-pyridazino[1,2a][1,2]diazepine-1-formoyl]-L-aspartic acid aldehyde;

[9-(2-Pyridinoylamino)octahydro-6,10-dioxo-6H-pyridazino[1,2a][1,2]diazepine-1-formoyl]-L-aspartic acid aldehyde; and

[9-(N-4-Methylpiperazinomethylbenzoylamino)octahydro-6,10-dioxo-6H-pyridazino[1,2a][1,2]diazepine-1-formoyl]-L-aspartic acid aldehyde.

21. A pharmaceutical composition for inhibiting interleukin-1β protease comprising a compound of the formula (A) defined in claim 1, in a pharmaceutically acceptable carrier.

22. A pharmaceutical composition comprising the compound defined in any of claims 2–15, in a pharmaceutically acceptable carrier.

23. A pharmaceutical composition comprising the compound according to claim 1 selected from the group consisting of:

[9-(Benzyloxycarbonylamino)octahydro-6,10-dioxo-6H-pyridazino[1,2a][1,2]diazepine-1-formoyl]-L-aspartic acid 2,6-dichlorobenzoyloxymethyl ketone;

[9-(4-Dimethylaminomethylbenzoylamino)octahydro-6,10-dioxo-6H-pyridazino[1,2a][1,2]diazepine-1-formoyl]-L-aspartic acid 2,6-dichlorobenzoyloxymethyl ketone;

[9-(N-[4-Methylpiperazinomethyl]benzoylamino)octahydro-6,10-dioxo-6H-pyridazino[1,2a][1,2]diazepine-1-formoyl]-L-aspartic acid 2,6-dichlorobenzoyloxymethyl ketone;

[9-(4-(N-Methylpiperazinylmethyl)benzoylamino)octahydro-6,10-dioxo-6H-pyridazino[1,2a][1,2]diazepine-1-formoyl]-L-aspartic acid 2,6-dichlorobenzoyl-oxymethyl ketone; and

[9-(4-(N-(2-Methyl)imidazolylmethyl)benzoylamino)octahydro-6,10-dioxo-6H-pyridazino [1,2a][1,2]diazepine-1-formoyl]-L-aspartic acid 2,6-dichlorobenzoyloxymethyl ketone.

24. A pharmaceutical composition comprising the compound according to claim 1 selected from the group consisting of:

[9-(5-Benzimidazoylamino)octahydro-6,10-dioxo-6H-pyridazino[1,2a][1,2]diazepine-1-formoyl]-L-aspartic acid 2,6-dichlorobenzoyloxymethyl ketone;

[9 -(5-Bentriazoylamino)octahydro-6,10-dioxo-6H-pyridazino[1,2a][1,2]diazepine-1-formoyl]-L-aspartic acid 2,6-dichlorobenzoyloxymethyl ketone;

[9-(N-Carboethoxy-5-bentriazoylamino)octahydro-6,10-dioxo-6H-pyridazino[1,2a][1,2]diazepine-1-formoyl]-L-aspartic acid 2,6-dichlorobenzoyloxymethyl ketone;

[9-(N-Carboethoxy-5-benzimidazoylamino)octahydro-6,10-dioxo-6H-pyridazino[1,2a][1,2]diazepine-1-formoyl]-L-aspartic acid 2,6-dichlorobenzoyloxymethyl ketone; and

[9-(Benzyloxycarbonylamino)octahydro-10-oxo-6H-pyridazino[1,2a][1,2]diazepine-1-formoyl]-L-aspartic acid 2,6-dichlorobenzoyloxymethyl ketone.

25. A pharmaceutical composition comprising the compound according to claim 1 selected from the group consisting of:

[9-(4-Dimethylaminomethylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-phenyl-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone; and

[9-(Benzoylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone.

26. A pharmaceutical composition comprising the compound according to claim 1 selected from the group consisting of:

[9-(4-Carboxymethylthiobenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(4-Carboxyethylthiobenzoylamino)octahydro-6,10-dioxo-6H-pyridazino[1,2a][1,2]diazepine-1-formoyl]-L-aspartic acid 5 -(1-(4-chlorophenyl)-3-trifluoromethyl) pyrazoloxymethyl ketone;

[9-(Isobutyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(4-Carboxyethylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl)-pyrazoloxymethyl ketone;

[9-(4-Carboxypropylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(4-chloro-2-pyridinyl)-3-trifluoromethyl) pyrazoloxymethyl ketone; and

[9-(4-Dimethylaminomethylbenzoylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone.

27. A pharmaceutical composition comprising the compound according to claim 1 selected from the group consisting of:

[9-(Benzyloxycarbonylamino)octahydro-6,10-dioxo-6H-pyridazino[1,2a][1,2]diazepine-1-formoyl]-L-aspartic acid aldehyde;

[9-(Benzoylamino)octahydro-6,10-dioxo-6H-pyridazino[1,2a][1,2]diazepine-1-formoyl]-L- aspartic acid aldehyde;

[9-(4-Carboxymethoxybenzoylamino)octahydro-6,10-dioxo-6H-pyridazino[1,2a][1,2]diazepine-1-formoyl]-L-aspartic acid aldehyde;

[9-(2-Fluorobenzoylamino)octahydro-6,10-dioxo-6H-pyridazino[1,2a][1,2]diazepine-1-formoyl]-L-aspartic acid aldehyde;

[9-(2-Pyridinoylamino)octahydro-6,10-dioxo-6H-pyridazino[1,2a][1,2]diazepine-1-formoyl]-L-aspartic acid aldehyde; and

[9-(N-4-Methylpiperazinomethylbenzoylamino)octahydro-6,10-dioxo-6H-pyridazino[1,2a][1,2]diazepine-1-formoyl]-L-aspartic acid aldehyde.

28. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound of the formula (A) or a pharmaceutically acceptable salt thereof:

wherein:

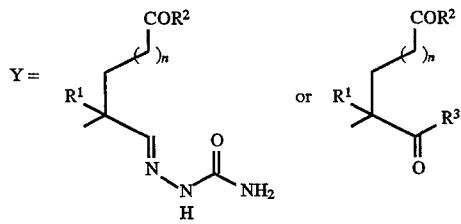

and when $R^2$=OH then Y can also be equal to:

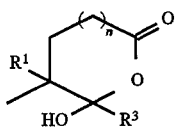

wherein
n=0,1;
$R^1$=H or deuterium;
$R^2$=$OR^4$ or NHOH;
$R^4$=H, alkyl, cycloalkyl, aralkyl;
$R^3$=H, $(CR^8R^9)_{0-6}CF_3$, $(CR^8R^9)_{0-6}CF_2CF_3$, $(CR^8R^9)_{0-6}COOR^5$, $(CR^8R^9)_{0-6}CONR^6R^7$, $CF_2(CR^8R^9)_{0-6}$aryl, $CF_2(CR^8R^9)_{0-6}$heteroaryl, $CF_2(CR^8R^9)_{0-6}$alkyl, $CHN_2$,$CH_2R^{10}$, $COR^5$;
wherein
$R^5$=H, alkyl, cycloalkyl, aryl, aralkyl, heteroaryl, heteroaralkyl;
$R^6$ and $R^7$ are independently selected from H, alkyl, cycloalkyl, aryl, aralkyl, heteroaryl, heteroaralkyl and where $R^6$ and $R^7$ are taken together can be a 3-,4-,5-,6- or 7-membered carbocyclic ring;
$R^8$ and $R^9$ are independently H, or alkyl;
$R^{10}$=alkyl, aryl, aralkyl, heteroaryl, heteroarakyl, H, halo, $SR^5$, $SR^5R^6$, $O(CO)_{0-1}$aryl, $O(CO)_{0-1}$heteroaryl, OP(O) $R^{11}R^{12}$,

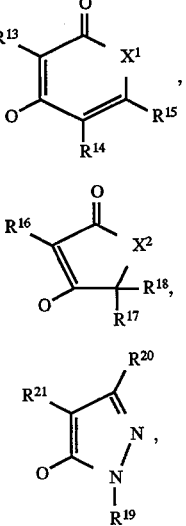

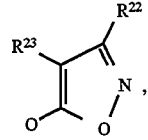

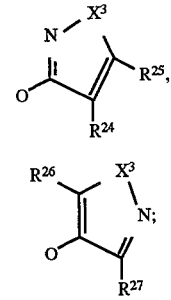

$R^{11}$ and $R^{12}$ are optionally selected from H, OH, alkyl, cycloalkyl, aryl, aralkyl, heteroaryl, heteroaralkyl, alkoxy, aroxy, aralkyloxy, heteroaroxy, heteroaralkyloxy;
$R^{13}$=H, alkyl, aryl, aralkyl;
$R^{14}$ and $R^{15}$ are optionally selected from H, alkyl, aryl, or when taken together $R^{14}$ and $R^{15}$ is an aryl ring;
$X^1$=O, S, $NR^{28}$ where $R^{28}$=H, alkyl, aryl, aralkyl, heteroaryl, heteroaralkyl;
$R^{16}$=H, Cl, alkyl, $(CR^8R^9)_{0-6}$-aryl;
$R^{17}$ and $R^{18}$ are independently H or alkyl;
$X^2$=$CH_2$, O, $NR^{28}$;
$R^{19}$=H, alkyl, cycloalkyl, alkylcycloalkyl, aryl, aralkyl, heteroaryl and heteroaralkyl;
$R^{20}$=H, alkyl, $CF_3$, $CF_2,CF_3$, $COOR^5$, $CONR^6R^7$, cycloalkyl, alkylcycloalkyl, aryl, aralkyl, heteroaralkyl, heteroaryl and where $R^{21}$=H or alkyl;
$R^{22}$, $R^{23}$, $R^{24}$, $R^{25}$, $R^{26}$, and $R^{27}$ are independently selected from H, alkyl, cycloalkyl, alkylcycloalkyl, aryl, aralkyl, heteroaryl, heteroaralkyl and $R^{29}$; and where $R^{24}$ and $R^{25}$ when taken together may be aryl or heteroaryl;
$X^3$=O,S;
$R^{29}$=F, Cl, $CF_3$, $CF_2CF_3$, $(CF_2)_{0-3}$—H, $COOR^5$, $CONR^{30}R^{31}$, where $R^{30}$ and $R^{31}$ are optionally selected from $R^6$ and $R^7$,

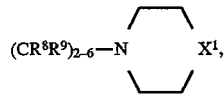

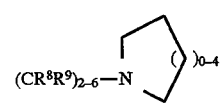

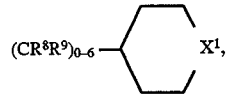

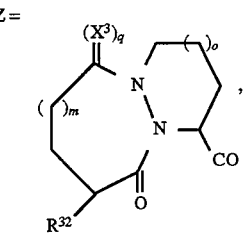

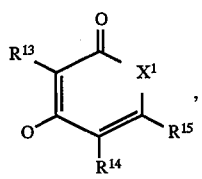

-continued

[chemical structures with R32, R33, R34, X4, R35, R36, etc.]

wherein
q=0,1;
m=0,1,2,3;
o=0,1,2;
X⁴=H, alkylthio;

[structure with R32=]

$R^{33}$ and $R^{34}$ are optionally H, alkyl, aryl or when taken together, $R^{33}$ and $R^{34}$ are aryl, heteroaryl, or a double bond; $R^{35}$ and $R^{36}$ are optionally an oxygen atom or no bond; $R^{37}$=H, alkyl;
$R^{38}$=independently selected from H, alkyl, aryl, aralky, heteroaryl, heteroaralkyl, $R^{40}$—$SO_2$, $R^{41}$—CO, $R^{50}$O—CO, $R^{51}NR^5$—CO;

wherein $R^{40}$=$R^5$ or $HNR^5$;
$R^{41}$=alkenyl, aralkenyl, heteroaralkenyl, alkynyl, aralkynyl, heteroaralkynyl, $R^{42}$—$OCOR^5$, $R^{43}$—$COR^5$, $R^{42}$—$NR^{47}C(=NR^6)R^5$, $R^{42}$—$NR^{47}(=NR^6)NR^5$, $R^{42}$—$SR^5$, $R^{42}$—$S(CR^8R^9)_{1-6}COOR^{47}$, $R^{42}$—$S(CR^8R^9)_{1-6}COONR^{47}R^{48}$, $R^{42}$—$OR^5$, $R^{42}$—$O(CR^8R^9)_{1-6}COOR^{47}$, $R^{42}$—$O(CR^8R^9)_{1-6}COONR^{47}R^{48}$, $R^{42}$—$NR^5SO_2R^6$, $R^{43}$—$R^{44}$, $R^{43}$—$R^{45}$, $R^{43}$—$R^{46}$, $R^{43}$—$NR^{47}R^{48}$, $R^{42}$—OH, $R^{43}$—$CF_3$;
wherein $R^{42}$=$(CR^8R^9)_{1-7}$ and $R^{43}$=$(CR^8R^9)_{0-6}$;
$R^{44}$=H, alkyl, —$(CH_2)_{0-4}$-cycloalkyl;

[structures with —$(CH_2)_{0-4}$ rings]

aryl, heteroaryl, aralkyl, heteroaralkyl, —$(CH_2)_{2-6}$—$R^{49}$;
wherein p=1–4;
$R^{49}$=alkoxy, $CH_2F$, $CHF_2$, $CF_3$, $CF_2CF_3$, OH, $COOR^{47}$, $CONR^{47}R^{48}$, or $NR^{47}R^{48}$;
wherein $R^{48}$ is independently H, alkyl, aryl, aralkyl, heteroaryl, heteroaralkyl, $CH_2CH_2O$-alkyl and C(O)—$R^{49}$;
$R^{47}$ is independently H, alkyl, cycloalkyl, aryl, aralkyl, heteroaryl and heteroaralkyl;
and when $R^{47}$ and $R^{48}$ are taken together, they can equal a five, six or seven membered ring of the type:

[ring structure]

where p=1–4 and n=0–1;
$R^{49}$ is alkyl, aryl, aralkyl, heteroaryl and heteroaralkyl;

$R^{45}$ = —N⟨ ⟩$X^1$ and —N⟨ ⟩S;

$R^{46}$ = [ring O] and [ring $NR^{28}$], where p=1–4;
$R^{50}$ and $R^{51}$=independently selected from alkyl, $R^{43}$-cycloalkyl, aryl, aralkyl, heteroaryl, heteroaralkyl, $R^{42}$-alkenyl, $R^{42}$-heteroaralkenyl, $R^{42}$-alkynyl, $R^{42}$-aralkynyl, $R^{42}$-heteroaralkynyl, $R^{43}$—$R^{46}$, $R^{42}$—$R^{49}$, $R^{52}$—$R^{45}$, $R^{42}$—$COOR^{47}$, $R^{42}$—$CONR^{47}R^{48}$, $R^{52}$—$OCOR^5$, $R^{52}$—$COR^5$, $R^{52}$—$NR^{47}C(=NR^6)R^5$, $R^{52}$—$NR^{47}(=NR^6)NR^5$, $R^{52}$—$SR^5$, $R^{52}$—$S(CR^8R^9)_{1-6}COOR^{47}$, $R^{52}$—$S(CR^8R^9)_{1-6}COONR^{47}R^{48}$, $R^{52}$—$OR^5$, $R^{52}$—$O(CR^8R^9)_{1-6}COOR^{47}$, $R^{52}$—$O(CR^8R^9)_{1-6}COONR^{47}R^{48}$, $R^{52}$—$NR^5SO_2R^6$, $R^{52}$—$R^{44}$, $R^{52}$—$NR^{47}R^{48}$,
where $R^{52}$=$(CR^8R^9)_{2-6}$.

29. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound defined in any of claims 2–15.

30. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound selected from the group consisting of:

[9-(Benzyloxycarbonylamino)octahydro-6,10-dioxo-6H-pyridazino[1,2a][1,2]diazepine-1-formoyl]-L-aspartic acid 2,6-dichlorobenzoyloxymethyl ketone;

[9-(4-Dimethylaminomethylbenzylamino)octahydro-6,10-dioxo-6H-pyridazino[1,2a][1,2]diazepine-1-formoyl]-L-aspartic acid 2,6-dichlorobenzoyloxymethyl ketone;

[9-(N-[4-Methylpiperazinomethyl]benzylamino)octahydro-6,10-dioxo-6H-pyridazino[1,2a][1,2]diazepine-1-formoyl]-L-aspartic acid 2,6-dichlorobenzoyloxymethyl ketone;

[9-(4-(N-Methylpiperazinylmethyl)benzoylamino)octahydro-6,10-dioxo-6H-pyridazino[1,2a][1,2]diazepine-1-formoyl]-L-aspartic acid 2,6-dichlorobenzoyl-oxymethyl ketone; and

[9-(4-(N-(2-Methyl)imidazolylmethyl)benzoylamino)octahydro-6,10-dioxo-6H-pyridazino [1,2a][1,2]diazepine-1-formoyl]-L-aspartic acid 2,6-dichlorobenzoyloxymethyl ketone.

31. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound selected from the group consisting of:

[9-(5-Benzimidazoylamino)octahydro-6,10-dioxo-6H-pyridazino[1,2a][1,2]diazepine-1-formoyl]-L-aspartic acid 2,6-dichlorobenzoyloxymethyl ketone;

[9-(5-Bentriazoylamino)octahydro-6,10-dioxo-6H-pyridazino[1,2a][1,2]diazepine-1-formoyl]-L-aspartic acid 2,6-dichlorobenzoyloxymethyl ketone;

[9-(N-Carboethoxy-5-bentriazoylamino)octahydro-6,10-dioxo-6H-pyridazino[1,2a][1,2]diazepine-1-formoyl]-L-aspartic acid 2,6-dichlorobenzoyloxymethyl ketone;

[9-(N-Carboethoxy-5-benzimidazoylamino)octahydro-6,10-dioxo-6H-pyridazino[1,2a][1,2]diazepine-1-formoyl]-L-aspartic acid 2,6-dichlorobenzoyloxymethyl ketone; and

[9-(Benzyloxycarbonylamino)octahydro-10-oxo-6H-pyridazino[1,2a][1,2]diazepine-1-formoyl]-L-aspartic acid 2,6-dichlorobenzoyloxymethyl ketone.

32. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound selected from the group consisting of:

[9-(4-Dimethylaminomethylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-phenyl-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone; and

[9-(Benzoylamino)octahydro-6,10-dioxo-6H-pyridazino[1,2a][1,2]diazepine-1-formoyl]-L-aspartic acid 5-(1-(4-chlorophenyl)-3-trifluoromethyl)pyrazoloxymethyl ketone.

33. A method for inhibiting interleukin-1β protease activity in a mammal in need of treatment for inflammatory and immune-based diseases of lung, central nervous system, and connective tissue comprising administering to said mammal an effective interleukin-1β inhibitory amount of a composition comprising a compound selected from the group consisting of:

[9-(4-Carboxymethylthiobenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(4-Carboxyethylthiobenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Isobutyloxycarbonylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(4-Carboxyethylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl)-pyrazoloxymethyl ketone;

[9-(4-Carboxypropylbenzoylamino)octahydro-6,10-dioxo-6H-pyridazino[1,2a][1,2]diazepine-1-formoyl]-L-aspartic acid 5-(1-(4-chlorophenyl)-3-trifluoromethyl) pyrazoloxymethyl ketone;

[9-(Benzyloxycarbonylamino)octahydro-6,10-dioxo-6H-pyridazino[1,2a][1,2]diazepine-1-formoyl]-L-aspartic acid 5-(1-(4-chloro-2-pyridinyl)-3-trifluoromethyl) pyrazoloxymethyl ketone; and

[9-(4-Dimethylaminomethylbenzoylamino)octahydro-6,10-dioxo-6H-pyridazino[1,2a][1,2]diazepine-1-formoyl]-L-aspartic acid 5-(1-(2-pyridinyl)-3-trifluoromethyl) pyrazoloxymethyl ketone.

\* \* \* \* \*